United States Patent
Mattson et al.

[11] Patent Number: 6,153,611
[45] Date of Patent: *Nov. 28, 2000

[54] PIPERAZINYL-CYCLOHEXANES AND CYCLOHEXENES

[75] Inventors: Ronald J. Mattson, Meriden; John D. Catt, Southington, both of Conn.

[73] Assignee: Bristol-Myers Squibb Company, Princeton, N.J.

[*] Notice: This patent is subject to a terminal disclaimer.

[21] Appl. No.: 08/083,752

[22] Filed: Jun. 25, 1993

Related U.S. Application Data

[63] Continuation-in-part of application No. 07/848,767, Mar. 11, 1992, abandoned.

[51] Int. Cl.[7] .................. A61K 31/496; C07D 295/073; C07D 295/096; C07D 405/10
[52] U.S. Cl. .................. 514/252.12; 514/253.01; 514/253.06; 514/254.09; 514/254.1; 514/254.11; 514/254.02; 514/317; 514/318; 514/321; 514/323; 514/326; 544/360; 544/363; 544/364; 544/368; 544/372; 544/373; 544/377; 544/378; 544/379; 544/398; 544/403; 546/192; 546/193; 546/197; 546/200; 546/201
[58] Field of Search .................. 544/360, 363, 544/364, 368, 372, 373, 377, 378, 379, 398, 403; 514/252, 253, 255

[56] References Cited

U.S. PATENT DOCUMENTS

| | | | |
|---|---|---|---|
| 3,960,961 | 6/1976 | Lednicer | 544/403 |
| 4,954,502 | 9/1990 | Smith et al. | 514/253 |
| 4,957,921 | 9/1990 | Caprathe et al. | 544/360 |
| 4,975,445 | 12/1990 | Caprathe et al. | 544/360 |
| 5,124,457 | 6/1992 | Ungemach et al. | 544/375 |

OTHER PUBLICATIONS

Lobner et al, *Neurosci. Lett. 117*, p. 169 (1990).
Rao et al, *Neuropharmacology, 29*p. 1199 (1990).
Treiber et al, Chemical Abstracts, vol. 118, No. 80952 (1993) (Abstract for DE 4108527, Sept. 17, 1992).

*Primary Examiner*—Emily Bernhardt

[57] ABSTRACT

Novel non-dopaminergic antiischemic compounds have Formula I:

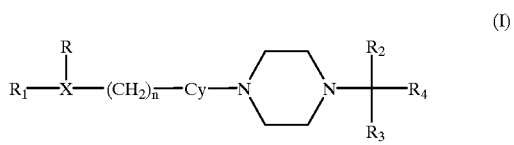

wherein
R=$R_1$ and is independently H, $C_{1-4}$ alky $C_{1-4}$ alkoxy, $C_{1-4}$ trihaloalkyl or halogen, or R and $R_1$ may be taken together to form an —O(CH$_2$)$_m$O— (m=1 or 2);
X=a 3-indolyl, phenyl, naphthalenyl or 2-benzothiazolyl residue;
n=0, 1, 2 or 3;

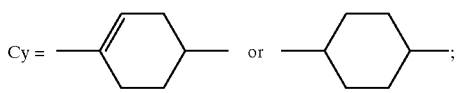

$R_2$=$R_3$ and is independently H or $C_{1-4}$ alkyl; and
$R_4$=phenyl, 2-thienyl, 2-quinolinyl, 4-pyridinyl or substituted phenyl.

20 Claims, No Drawings

PIPERAZINYL-CYCLOHEXANES AND CYCLOHEXENES

This application is a continuation-in-part of U.S. Ser. No. 07/848,767, filed Mar. 11, 1992, and now abandoned.

BACKGROUND

This invention generally pertains to piperazinyl- and piperidinyl-cyclohexenes and analogous cyclohexanes having anti-ischemic, antipsychotic and other bio-affecting properties and to their preparation and use. In some preferred embodiments, the invention is concerned with 1,4-disubstituted piperazine or piperidine derivatives wherein the 4-substituent is benzyl or substituted benzyl, and the 1-substituent is a 1-aryl-cyclohexen-4-yl or a 1-aryl-cyclohexan-4-yl moiety. These compounds and others structurally related thereto possess a unique profile that makes them useful in the treatment of ischemia-induced illnesses and psychosis.

Caprathe et al. disclosed a series of piperazinyl-cyclohexene compounds characterized by structural formula A in U.S. Pat. No. 4,975,445. Formula A is:

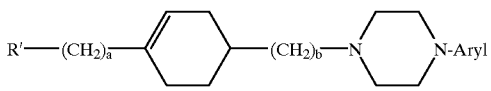

(A)

wherein R' is an aryl or heterocyclic ring, a is 0–2 and b is 0–4.

As can be seen, these earlier compounds are chemically distinguishable from the instant compounds on the basis of their chemical structures because they are aryl- or heteroaryl-piperazines, whereas the instant compounds are benzyl- or heteroarylmethyl-piperazines (when, in Formula I below, Y=N) or -piperidines (when, in Formula I below, Y=CH). Additionally, these earlier compounds are biologically distinguishable from the instant compounds, since the earlier compounds possess dopaminergic properties, which are associated with undesirable side effects including Parkinsonism and extrapyramidal side effects such as catalepsy. Contrastingly, the instant compounds are devoid of dopaminergic properties and the movement disorders often associated therewith.

U.S. Pat. No. 4,954,502 to Smith et al discloses compounds of the following formula:

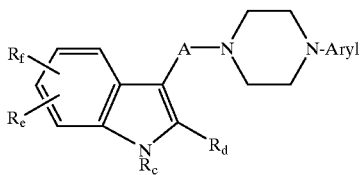

wherein A may be a $C_{5-7}$ cycloalkyl ring. The compounds are taught to be antidepressants. There is no suggestion in the patent that these compounds are useful in the treatment of stroke or other ischemia-based conditions.

Caprathe et al disclosed a series of piperazinyl-cyclohexanol compounds characterized by structural formula B in U.S. Pat. No. 4,957,921. Formula B is:

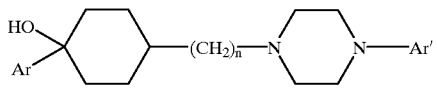

(B)

wherein n is 0 to 4 and Ar and Ar' are aryl or heterocyclic rings. Likewise, these compounds are structurally and biologically distinguishable from the instant compounds. Chemically, the reference compounds are aryl-piperazines, while the instant compounds are benzyl- or heteroarylmethyl-piperazines. Biologically, their dopaminergic properties distinguish them from applicants' compounds, which do not have dopaminergic activity. Accordingly, the movement disorders associated with dopaminergic agents are avoided when the instant compounds are administered.

SUMMARY AND DETAILED DESCRIPTION OF THE INVENTION

In its broadest aspect, the invention is concerned with certain non-dopaminergic compounds which are substituted benzyl- or heteroarylmethyl-piperazinyl cyclohexenes or substituted benzyl or heteroarylmethyl piperidinyl cyclohexenes which are useful anti-ischemic and antipsychotic agents. The compounds conform to formula I:

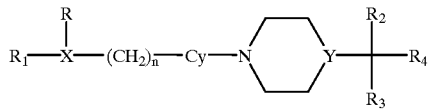

(I)

wherein $R=R_1$ and is independently H, $C_{1-4}$ alkyl, $C_{1-4}$ alkoxy, $C_{1-4}$ trihaloalkyl or halogen, or R and $R_1$ may be taken together to form an —$O(CH_2)_mO$— (m=1 or 2);

X=an indolyl, phenyl, naphthalenyl or 2-benzothiazolyl residue;

n=0, 1, 2 or 3;

Cy=a 1-cyclohexenyl or cyclohexyl residue (with the C=C of cyclohexene linked to $CH_2$ or to X);

Y=N or CH;

$R_2=R_3$ and is independently H or $C_{1-4}$ alkyl;

$R_4$=phenyl, 2-thienyl, 2-quinolinyl, 4-pyridinyl or substituted phenyl, wherein the phenyl group is mono-, di- or tri-substituted with groups selected from: F, Br, Cl, I and $C_{1-4}$ alkoxy.

Compounds of formula I include all pharmaceutically acceptable salts and/or solvates (e.g., hydrates) thereof. The invention also encompasses all stereoisomers of compounds of formula I.

Pharmaceutically acceptable salts based on Formula I can be obtained using inorganic or organic acids such as oxalic, sulfuric, phosphoric, hydrochloric, hydrobromic, hydroiodic, citric, acetic, benzoic, fumaric, cinnamic, mandelic, nitric, mucic, isethionic, palmitic, heptanoic and the like.

R and $R_1$ may be H or a $C_{1-4}$ alkyl, $C_{1-4}$ alkoxy, $C_{1-4}$ trihaloalkyl or halogen moiety. When R is not H, it is generally preferred that it be an alkyl, alkoxy or trihaloalkyl group containing one carbon atom. Preferred groups of this type are methyl, methoxy and trifluoromethyl groups.

Another preferred group of R substituents are halogen atoms. While R may be Cl, Br, I or F, it is highly preferred that it be F.

R and $R_1$ may be taken together to form an —O(CH$_2$)$_m$O— (m=1 or 2) moiety.

X is an aryl or heteroaryl group. X may be any of a wide variety of groups containing from 6 to 10 carbon atoms and optionally, one or more hetero atoms, such as N, O and S in mono- or polycyclic or bridged ring systems. Preferred X groups are: indolyl, phenyl, naphthalenyl and 2-benzothiazolyl.

n is 0, 1, 2 or 3. It is preferred that n be 0 or 1.

Cy is a cyclohexene or cyclohexane residue aligned in the structure so that it appears as a

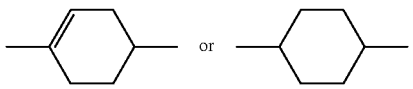

radical. If Cy is a cyclohexenyl group, the double bond involves the C which is linked to X or CH$_2$.

Y may be N or CH. While it may be either, the use of piperidines (wherein Y=CH) is preferred.

$R_2$ and $R_3$ may each independently be selected from H and $C_{1-4}$ alkyl groups.

$R_4$ may be any of a variety of aryl residues derived from a phenyl or heteroaryl moiety. Useful heteroaryl groups include phenyl, 4-pyridinyl, and 2-quinolinyl moieties. $R_4$ may also be a substituted phenyl group bearing 1, 2 or 3 substituents, with the substituents chosen from: F, Br, Cl, I and $C_{1-4}$ alkoxy.

One preferred class of compounds of Formula I are those in which X is a phenylene group. Of that class, those in which $R_4$ is a phenyl group are highly preferred.

Preferred compounds of Formula I include:

1-[4-(4-fluorophenyl)-3-cyclohexen-1-yl]-4-(phenylmethyl)piperazine,

1-[4-(4-fluoro-1-naphthalenyl)-3-cyclohexen-1-yl]-4-(phenylmethyl)piperazine,

1-[4-(1,3-benzodioxol-5-yl)-3-cyclohexen-1-yl]-4-(phenylmethyl)piperazine,

1-[4-(2-benzothiazolyl)-3-cyclohexen-1-yl]-4-phenylmethyl)piperazine,

1-[4-(4-methoxyphenyl)-3-cyclohexen-1-yl]-4-(phenylmethyl)piperazine, 1-(phenylmethyl)-4-[4-[4-(trifluoromethyl)phenyl]-3-cyclohexen-1-yl]piperazine, 1-[4-(4-fluorophenyl)-3-cyclohexen-1-yl]-4-[(4-fluorophenyl)methyl]piperazine, 1-[(4-fluorophenyl)methyl]-4-{4-[4-(trifluoromethyl)phenyl]-3-cyclohexen-1-yl}piperazine, 1-(phenylmethyl)-4-[4-(phenylmethyl)-3-cyclohexen-1-yl]piperazine, 1-[4-(4-fluorophenyl)-3-cyclohexen-1-yl]-4-(2-thienylmethyl)piperazine, 2{{4-[4-(4-fluorophenyl)-3-cyclohexen-1-yl]-1-piperazinyl]methyl]quinoline, 1-[4-(4-fluorophenyl)-3-cyclohexen-1-yl]-4-(4-pyridinylmethyl)piperazine, 1-[4-(4-fluorophenyl)-3-cyclohexen-1-yl]-4-(phenylmethyl)piperidine, 5-methoxy-3-{4-[4-(phenylmethyl)-1-piperazinyl]-1-cyclohexen-1-yl]-1H-indole, 5-fluoro-3-{4-[4-(phenylmethyl)-1-piperazinyl]-1-cyclohexen-1-yl]-1H-indole, 5-chloro-3-{4-[4-(phenylmethyl)-1-piperazinyl]-1-cyclohexen-1-yl]-1H-indole, 5-fluoro-3-{4-[4-(phenylmethyl)-1-piperidinyl]-1-cyclohexen-1-yl]-1H-indole, 1-[4-(1,3-benzodioxol-5-yl)-3-cyclohexen-1-yl]-4-[(3-methoxyphenyl)methyl]piperidine, 1-[4-(1,3-benzodioxol-5-yl)-3-cyclohexen-1-yl]-4-[(2-fluorophenyl)methyl]piperidine, 1-[4-(1,3-benzodioxol-5-yl)-3-cyclohexen-1-yl]-4-[(2,5-difluorophenyl)methyl]piperidine, 1-[4-(3,4-difluorophenyl)-3-cyclohexen-1-yl]-4-[(2,5-difluorophenyl)methyl]piperidine, 1-[4-(1,4-benzodioxan-6-yl)-3-cyclohexen-1-yl]-4-(phenylmethyl)piperazine, 1-[4-(1,3-benzodioxol-5-yl)-3-cyclohexen-1-yl]-4-[(2-chlorophenyl)methyl]piperazine, 1-[4-(1,3-benzodioxol-5-yl)-3-cyclohexen-1-yl]-4-[(2,5-difluorophenyl)methyl]piperazine, 1-[4-(1,3-benzodioxol-5-yl)-3-cyclohexen-1-yl]-4-[(3-methoxyphenyl)methyl]piperazine, 1-[(4-fluorophenyl)-3-cyclohexen-1-yl]-4-[(3-methoxyphenyl)methyl]piperazine, 1-[4-(1,3-benzodioxol-5-yl)-3-cyclohexen-1-yl]-4-[(2,5-diiodophenyl)methyl]piperazine, cis and trans 1-[4-(4-fluoro-1-naphthalenyl)-1-cyclohexyl]-4-(phenylmethyl)piperazine, trans 1-[4-(4-fluorophenyl)-1-cyclohexyl]-4-(phenylmethyl)piperazine, trans 2-{{4-[4-(4-fluorophenyl)-1-cyclohexyl]-1-piperazinyl]methyl]quinoline, trans 1-[4-(4-fluorophenyl)-1-cyclohexyl]-4-[(3-methoxyphenyl)methyl]piperazine and the like.

The compounds of the present invention are useful pharmacologic agents with anti-ischemic properties. Brain cells are particularly vulnerable to damage caused by ischemic conditions. Brain ischemia, or insufficient oxygen, may result from injury or disease and may last from only transient periods of time to periods of lengthy duration, as in stroke. In this regard, the compounds of Formula I are useful for treatment and prevention of injury to the brain and spinal cord and of edema due to head trauma, stroke, arrested breathing, cardiac arrest, Reyes syndrome, cerebral thrombosis, embolism, hemorrhage or tumors, encephalomyelitis, spinal cord injury, hydroencephalitis, and post-operative brain injury.

By "non-dopaminergic", applicant's mean not exhibiting activity at dopamine ($D_2$) receptor sites. Activity at $D_2$ sites is measured using the screening process set out in Example 67. Compounds of formula I which have $IC_{50}$ values greater than 1,000 nM in this test are non-dopaminergic and, therefore, within the scope of the instant claims.

TABLE 1

Anti-ischemic Compounds of Formula I which are Dopaminergic

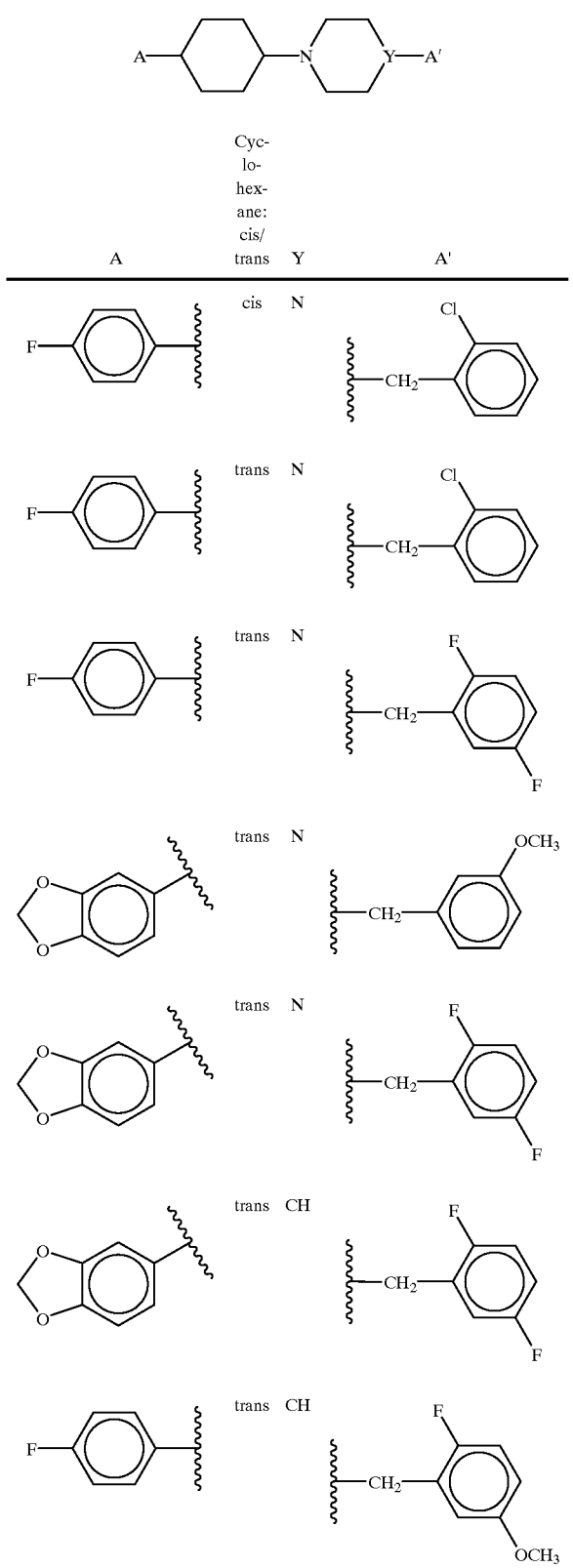

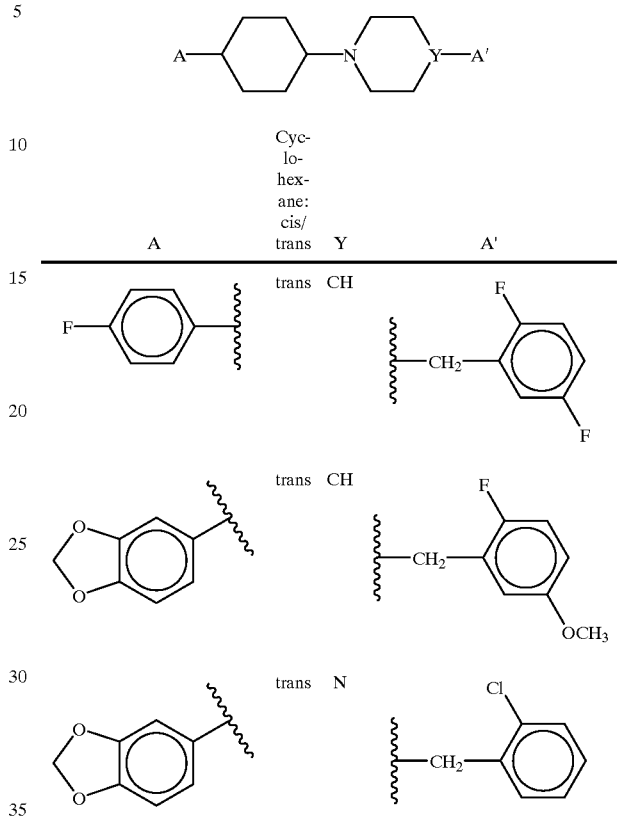

The anti-ischemic activity of the compounds of Formula I has been demonstrated in certain pharmacological tests and model systems that are used to determine drug effects on brain ischemia and its aftermath. Most specifically, administration of the compounds of Formula I results in protection against hypoxia-induced death in an anoxic nitrogen test in rats (Example 66). The test identifies the neuro-protective effects of substances against lethal brain damages produced by a lack of oxygen consumption (anoxia). In this test procedure, control animals exposed for one minute to a pure nitrogen atmosphere will expire because of respiratory failure caused by irreversible damage to the brain respiratory center. To demonstrate effectiveness, experimental compounds must antagonize the anoxic insult, increasing the survivability of the test animals.

One aspect of the present invention provides a method for treating a mammal suffering from ischemia or being susceptible to ischemia, which comprises administering systematically to said mammal a therapeutically effective amount of a compound of Formula I or a pharmaceutically acceptable acid addition salt thereof.

Although the dosage and dosage regimen must in each case be carefully adjusted, utilizing sound professional judgement and considering the age, weight and condition of the recipient, the route of administration and the nature and gravity of the illness, generally the daily dose will be from about 0.01 to about 10 mg/kg, preferable 0.1 to 2 mg/kg, when administered parenterally and from about 1 to 50 mg/kg, when administered orally. In some instances a sufficient therapeutic effect can be obtained at lower doses while in others, greater doses will be required.

Systemic administration refers to oral, rectal, transnasal, transdermal, and parenteral (i.e., intramuscular, intravenous, and subcutaneous). Generally it will be found that when a compound is administered orally, a greater quantity of the active agent is required to produce the same effect as a similar quantity given parenterally. According to good clinical practice, it is preferred to administer the present compounds at a concentration level that will produce effective anti-ischemic effects without causing any harmful or untoward side effects.

The compounds of the present invention may be administered for anti-ischemic or antipsychotic purposes either as individual therapeutic agents or as mixtures with other therapeutic agents. Therapeutically, they are generally given as pharmaceutical compositions composed of an anti-ischemic or antipsychotic amount of a compound of Formula I or a pharmaceutically acceptable salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs, and aqueous solutions.

The nature of the pharmaceutical composition employed will, of course, depend on the desired route of administration. For example, oral compositions may be in the form of tablets or capsules and may contain conventional excipients such as binding agents (e.g., starch) and wetting agents (e.g., sodium lauryl sulfate). Solutions or suspensions of a Formula I compound with conventional pharmaceutical vehicles are employed for parenteral compositions such as aqueous solution for intravenous injection or an oily suspension for intramuscular injection.

Compounds of Formula I can be prepared by the processes set out in the following schemes:

The intermediate substituted cyclohexanones, iii, were prepared by condensation of cyclohexane-1,4-dione monoethylene ketal with a 1-arylmethylpiperazine or a 4-arylmethylpiperidine under reductive alkylation conditions such as titanium (IV) isopropoxide/$NaBH_4$, sodium cyanoborohydride, sodium triacetoxyborohydride and the like as shown in Scheme 1. The resulting ketals are cleaved under acidic conditions such as, acetone/HCl, THF/HCl, ethanol/HCl, ethanol/$H_2SO_4$, HCl, acetone/$H_2SO_4$, THF/$H_2SO_4$, and the like. Other methods known to those skilled in the art may also be used.

The further addition of organometallic reagents such as, Grignard reagents or organolithium reagents and the like to the intermediates, iii, provides the 1-aryl(alkyl)-4-(arylmethyl-1-piperazinyl)cyclohexanols and the 1-aryl(alkyl)-4-(arylmethyl-1-piperidinyl)cyclohexanols, iv, as mixtures of diastereomers. The reaction may be carried out in an appropriate solvent such as tetrahydrofuran, diethyl ether, dimethoxyethane, diethyleneglycol dimethyl ether and the like, at temperatures from −100 to 25° C. The positional isomers, iv, may be separated and the individual isomers reacted separately or the diastereomer mixture may be used in the following procedure. Means for separation of the positional isomers, iv, include but are not limited to, recrystallization, chromatographic separation using common absorbents such as silica (silica gel), aluminum oxide (alumina) and the like.

Dehydration of the intermediates, iv, provides the compounds of formula i. Dehydration may be accomplished by heating with thionyl chloride, phosphorus oxychloride, thionyl bromide, phosphorus oxybromide, phosphorus trichloride, phosphorus tribromide, phosphorus pentachloride, phosphorus tribromide and the like in an inert solvent such as dichloromethane, 1,2-dichloroethane, chloroform, carbon tetrachloride, benzene, cyclohexane and the like at temperatures of 20 to 80° C. Additionally the dehydration may be accomplished by reacting with trifluoroacetic acid/trifluoroacetic anhydride, trifluoroacetic acid, phosphorus oxychloride/pyridine, para-toluenesulfonic acid/toluene, methanesulfonic acid/cyclohexane, sodium hydrogen sulfate/toluene, methanesulfonic acid/toluene and the like at temperatures from 0 to 110° C. Other methods for the dehydration of alcohols known to those skilled in the art may also be used. Alternatively, the crude cis/trans mixture from the reaction of the organometallic reagent and the 4-(4-arylmethyl-1-piperazinyl)cyclohexanones and 4-(4-arylmethyl-1-piperidinyl)-cyclohexanones may be dehydrated directly under acidic conditions as described above.

SCHEME 2:

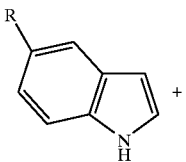
+

SCHEME 1:

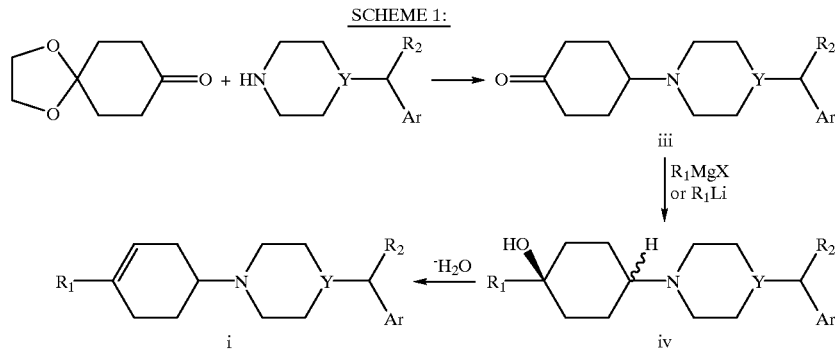

-continued

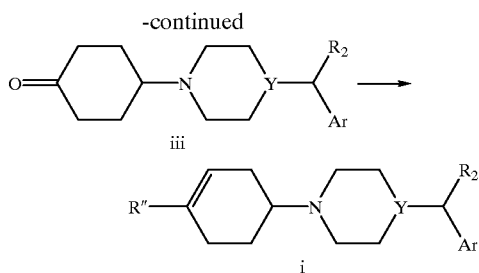

The 1-(4-indolyl-3-cyclohexen-1-yl)-4-(arylmethyl)-piperazines and 1-(4-indolyl-3-cyclohexen -1-yl)-4-arylmethylpiperidines I (R"=3-indolyl) may be prepared (Scheme 2) by condensing the intermediates, iii, with the appropriately substituted indole in a suitable solvent such as ethanol, methanol, 2-propanol, tetrahydrofuran, toluene, dimethoxyethane, acetonitrile, and the like, with basic catalysts such as pyrrolidine, piperidine, and the like, at temperatures from 30° to 110° C. Alternatively, the condensation may be accomplished using acidic catalysts in a suitable solvent.

benzenesulfonyl, para-toluenesulfonyl, benzyl, appropriately substituted benzyl and the like. Highly preferred protecting groups are the t-butyl carbamate and the carbobenzyloxy group.

The intermediates, iva, are readily dehydrated and deprotected to provide the 1-[4-aryl(alkyl)-3-cyclohexen-1-yl] piperazines, ia, under conditions similar to those described above in Scheme 1. Highly preferred for this dehydration is treatment with trifluoroacetic acid which may result in simultaneous removal of the piperazine protecting group. Other methods for deprotection of the piperazine include, but are not limited to, acid hydrolysis, basic hydrolysis, hydrogenolysis, reductive cleavage and the like.

The 1-[4-aryl(alkyl)-3-cyclohexen-1-yl]-4-arylmethyl-piperazines, i, are prepared by alkylation of intermediate ia with such agents as arylmethyl halides, arylmethyl para-toluenesulfonates, arylmethyl methanesulfonates, and the like, in the presence a base in a suitable solvent such as acetonitrile, tetrahydrofuran, dioxane, acetone, 1,2-dichloroethane, dimethylformamide, dimethyl sulfoxide, and the like, at temperatures of 25° to 130° C. Suitable bases for this reaction include, but are not limited to, sodium or potassium carbonate, sodium or potassium bicarbonate,

SCHEME 3:

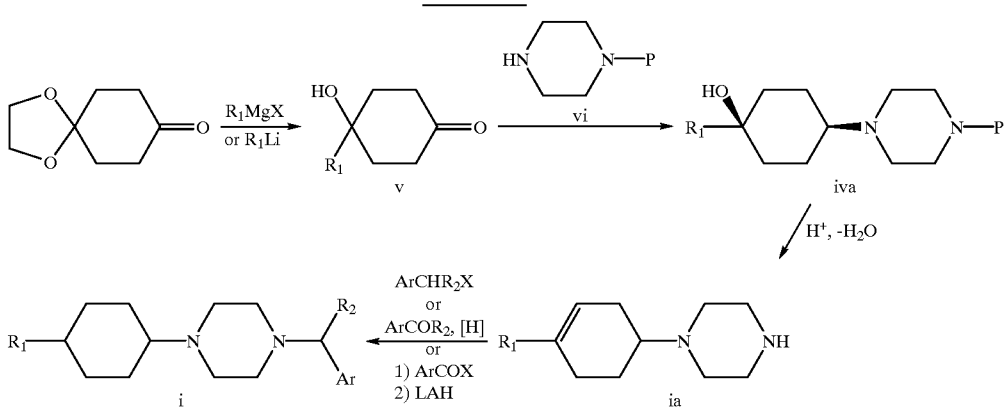

Scheme 3 shows an alternate synthesis of the compounds of formula i by way of intermediate ia. The intermediate substituted cyclohexanones v are obtained by addition of organometallic reagents such as Grignard reagents, organolithium reagents, and the like, to 1,4-cyclohexanedione mono-ethylene ketal. These reactions are generally carried out in solvents such as tetrahydrofuran, diethyl ether, dimethoxyethane, dioxane, ethylene glycol dimethyl ether and the like at temperatures from −80° to 30° C. The ketals are cleaved under acidic conditions in a solvent such as methanol, ethanol, 2-propanol, acetone, tetrahydrofuran, dioxane, dimethoxyethane, acetonitrile, dichloromethane, 1,2-dichloroethane and the like to give the 4-aryl(alkyl)-4-hydroxycyclohexanones v. Acids suitable for this hydrolysis include but are not limited to hydrochloric, sulfuric, acetic, dichloroacetic, trifluoroacetic, phosphoric, para-toluenesulfonic, methanesulfonic, benzoic and the like.

Intermediates, v, can be reductively coupled with a mono-protected piperazine, using conditions as described above in Scheme 1 for intermediates iv, to give the 1-protected piperazine intermediate, iva. Suitable protecting groups for the piperazine include but are not limited to carbobenzyloxy, ethyl carbamate, methyl carbamate, t-butyl carbamate, formyl, acetyl, propionyl, methanesulfonyl, ethanesulfonyl, sodium or potassium hydride, sodium or potassium hydroxide, diisopropylethylamine, pyridine, and the like.

Alternately, the 1-[4-aryl(alkyl)-3-cyclohexen-1-yl] piperazines ia may be reductively coupled with aryl aldehydes and aryl ketones to provide 1-[4-aryl(alkyl)-3-cyclohexen-1-yl]-1-arylmethylpiperazines i. Reagents suitable for this reductive coupling include but are not limited to sodium borohydride, sodium cyanoborohydride, sodium triacetoxyborohydride, sodium borohydride/titanium isopropoxide, sodium cyanoborohydride/titanium isopropoxide and the like. The reductively coupling is generally run in a solvent such as ethanol, methanol, tetrahydrofuran, dioxane, dichloromethane, 1,2-dichloroethane, dimethoxyethane, and the like, at temperatures of 25 to 100° C.

The 1-[4-aryl(alkyl)-3-cyclohexen-1-yl]-1-arylmethylpiperazines, i, may also be prepared by coupling the intermediates, ia, with an aryl carboxylic acid derivative to furnish an aryl carboxamide, which can then be reduced to give the products, i. Typical acid derivatives include but are not limited to acid chlorides, esters, suitable amides such as those obtained from coupling reagents, e.g., carbonyl diimidazole, and the like. The carboxamides may be reduced with the usual reagents, which include but are not limited to lithium aluminum hydride, diisobutyl aluminum hydride, diborane, sodium bis(2-methoxyethoxy)aluminum hydride and the like. The reduction is typically carried out in a solvent such as tetrahydrofuran, diethyl ether, dioxane, benzene, toluene, cyclohexane, and the like, from temperatures of 0 to 120° C. Other methods known to those skilled in the arts for the preparation and reduction of amides may also be used.

SCHEME 4:

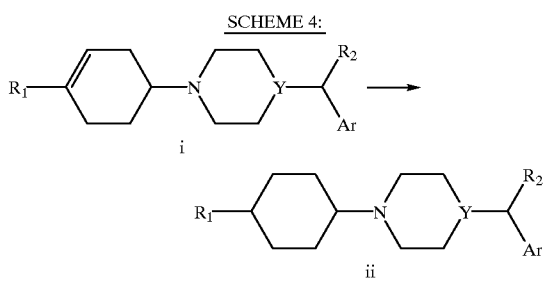

SCHEME 5

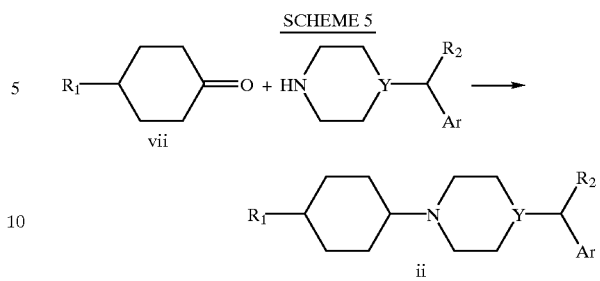

The intermediate 4-arylcyclohexanones, vii, (Lednicer et al, J. Med. Chem., 1975, 5, 1235), are condensed (Scheme 5) with the appropriately substituted piperazines or piperidines, in a manner similar to that previously described in Scheme 1, to provide the products, ii. The condensation provides isomeric mixtures of the products, ii, which are separated as previously described in Scheme 2.

SCHEME 6

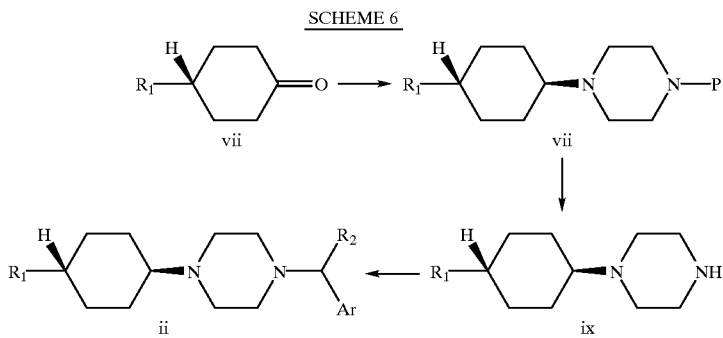

Reduction of the compounds, i, to provide the 1-[4-aryl-(alkyl)cyclohexyl]-4-(arylmethyl)piperazines and the 1-[4-aryl(alkyl)cyclohexyl]-4-(arylmethyl)-piperidines, ii, is shown in Scheme 4. This reduction may be accomplished either chemically or catalytically by means known to those skilled in the art. The preferred catalytic method is reduction with platinum oxide in acetic acid. Other catalysts suitable for this reduction include palladium on carbon, platinum on carbon, palladium hydroxide (Pearlman's catalyst), Raney nickel and rhodium on carbon in solvents such as methanol, ethanol, 2-propanol, acetic acid, dioxane, tetrahydrofuran, dimethylformamide, dimethoxyethane and the like at temperatures from 20 to 80° C. Typical chemical reducing agents for this reduction include, but are not limited to, $LiAlH_4$, $AlH_3$, borane, or complexes of borane with common tertiary amines and with common sulfides (methyl sulfide, ethyl sulfide, etc). The chemical reductions are generally carried out in solvents such as tetrahydrofuran, diethyl ether, dioxane, and the like at temperatures of 0 to 150° C. The products, ii, are obtained as mixtures of diastereomers which are separated as described in Scheme 1 above.

Alternate syntheses of the 1-[4-aryl(alkyl)cyclohexyl]-4-(arylmethyl)-piperazines and 1-[4-aryl(alkyl)-4-(arylmethyl)-cyclohexyl]piperidines, ii, are shown in Schemes 5 and 6.

Alternatively, the 1-[4-aryl(alkyl)cyclohexyl]-4-(arylmethyl)piperazines, ii, may be prepared by condensation of the 4-arylcyclohexanones, vii, with an appropriately protected piperazine, preferably 1-carbobenzyloxy or 1-t-butylcarboxy piperazine as shown in Scheme 6. Other suitable protecting groups for the piperazines include, but are not limited to, methyl carbamate, ethyl carbamate, acetyl, formyl, trityl, diphenylmethyl, benzyl, appropriately substituted benzyl.

The condensation provides diastereomeric mixtures of the intermediates, viii, which are deprotected to give the intermediates, ix. Methods suitable for deprotection include, but are not limited to, acidic or basic hydrolysis, hydrazinolysis, hydrogenolysis, solvolysis, and the like. intermediates, ix, can then be alkylated as described previously in Scheme 3 to give the products, ii.

EXAMPLES

The compounds which constitute this invention, their methods of preparation and their biological actions will be better appreciated after consideration of the following examples, which are given for the purpose of illustration only and are not be construed as limiting the invention. In the following examples, temperatures are expressed in degrees Celsius and melting points are uncorrected. Unless stated otherwise, all percentages given herein are weight percentages based on total composition weight.

The following examples describe in detail the preparation of compounds of Formula I, as well as Formula II synthetic intermediates in each process. It will be apparent to those skilled in the art that modifications, both of materials and methods, will allow preparation of other compounds disclosed herein.

A. Preparation of Formula II intermediate compounds

Some representative procedures for preparation of synthetic intermediate compounds utilized above are given herein below. Most starting materials and certain intermediates are either commercially available or procedures for their synthesis are readily available in the chemical literature, allowing their full utilization by one skilled in the art of organic synthetic chemistry.

Example 1

4-[4-(Phenylmethyl)-1-piperidinyl]cyclohexanone

Titanium(IV) isopropoxide (16.5 ml) was added to a mixture of 4-benzylpiperidine (8.76 g, 50 mmole) and 1,4-cyclohexanedione monoethylene ketal (7.81 g, 50 mmole) and heated gently. After stirring for 18 hr, the yellow oil was diluted with ethanol (100 ml) and $NaBH_4$ was added. The mixture was stirred for 4 hr and water (10 ml) was added to precipitate the $TiO_2$. The mixture was filtered and the filtrate concentrated in vacuo to give 15.87 g of the crude ketal intermediate as a tan solid. This intermediate was stirred in a mixture of THF (75 ml) and 50% $H_2SO_4$ for 20 hr. The acid was neutralized with NaOH (50%) and $Na_2CO_3$ with ice bath cooling. The ketone product was extracted with ether and concentrated in vacuo. This yellow oil was Kugelrohr distilled to give a colorless oil that solidified upon standing to give 8.30 g of the ketone as colorless crystals (61.5%).

Example 2

4-[4-(Phenylmethyl)-1-piperazinyl]cyclohexanone

Titanium isopropoxide (74 ml) was added to a mixture of 1-benzylpiperazine (35.2 g, 200 mmole) and 1,4-cyclohexanedione monoethylene ketal (31.2 g, 200 mmole). The mixture was then stirred until no ketone absorption was observed in the IR spectrum. The yellow oil was diluted with ethanol (200 ml) and sodium borohydride (7.6 g, 200 mmole) was added. The mixture was stirred for 16 hr and water (37 ml) of water was added to precipitate the $TiO_2$. The mixture was filtered and the filtrate was concentrated in vacuo. The residue was dissolved in ether and the solution washed with 1N HCl. The acid washes were basified with $K_2CO_3$ and the basic mixture extracted with methylene chloride. The extracts were dried over potassium carbonate and concentrated in vacuo to provide 56.5 g of ketal product which was stirred with a mixture of THF (300 ml) and 50% $H_2SO_4$ (300 ml) for 2 hr. The solution was diluted with water (500 ml) and carefully basified with $K_2CO_3$. The basic mixture was extracted with ether and the extracts dried over sodium sulfate. Concentration in vacuo and recrystallization from isopropyl ether gave the product (41 g, 71%, mp: 83–85° C.). Calc'd for $C_{17}H_{24}N_2O$: C, 74.97%; H, 8.89%; N, 10.29%. Found: C, 74.45%; H, 8.86%; N, 10.22%.

Example 3

8-(4-Fluorophenyl)-1,4-dioxaspiro[4.5]decan-8-ol

A solution of 1,4-cyclohexanedione monoethylene ketal (31.2 g, 200 mmole) in dry THF (250 ml) was added to a solution of 4-fluorophenylmagnesium bromide in dry THF at −60° C. The mixture was allowed to warm to 25° C. and quenched with saturated $NH_4Cl$ solution and extracted with ether. The extracts were dried with $Na_2SO_4$ and the solvent removed in vacuo. The residue was crystallized from hexane to give the product (89%, mp:133–135° C.). Calc'd for $C_{14}H_{17}FO_3$: C, 66.66%; H, 6.80%. Found: C, 66.54%; H, 7.12%.

Example 4

4-(4-Fluorophenyl)-4-hydroxycyclohexanone

A solution of 8-(4-fluorophenyl)-1,4-dioxaspiro[4.5]decan-8-ol (8.6 g, 36 mmole) in a mixture of 50% aqueous methanol and concentrated HCl (3 ml) was stirred for 78 hr. The methanol was removed in vacuo without heating and the residue extracted with ether. The extracts were dried with $Na_2SO_4$ and the solvent removed in vacuo to give the product (6.0 g, 86%, mp: 118–119° C.). Calc'd for $C_{12}H_{13}FO_2$: C, 69.22%; H, 6.30%. Found: C, 69.32%; H, 6.34%.

Example 5

8-(4-Fluorophenyl)-1,4-dioxaspiro[4.5]dec-7-ene

A mixture of 8-(4-fluorophenyl)-1,4-dioxaspiro[4.5]decan-8-ol (2.0 g, 7.9 mmole) and a catalytic amount of p-toluenesulfonic acid in 50 ml toluene was heated at reflux for 1.5 hr. The mixture was cooled and washed with saturated sodium bicarbonate solution. The toluene was removed in vacuo and the residue recrystallized from hexane to give the product (81%, mp: 84–85° C.). Calc'd for $C_{14}H_{15}FO_2$: C, 71.78%; H, 6.46%. Found: C, 71.33%; H, 6.33%.

Example 6

8-(4-Fluorophenyl)-1,4-dioxaspiro[4.5]decane

A mixture of 8-(4-fluorophenyl)-1,4-dioxaspiro[4.5]dec-7-ene (36.7 mmole) and platinum oxide (0.15 g) was hydrogenated in ethanol for 1.5 hr. The catalyst was removed by filtration and the ethanol removed in vacuo to give the product (100%, mp: 51–53° C.). Calc'd for $C_{14}H_{15}FO_2$: C, 71.17%; H, 7.26%. Found: C, 71.16%; H, 7.35%.

Example 7

4-(4-Fluorophenyl)cyclohexanone

Hydrochloric acid (0.75 ml) was added to a solution 8-(4-fluorophenyl)-1,4-dioxaspiro[4.5]decane (10 mmole) in methanol-water (2–1,100 ml). After stirring for 2 hr the methanol was removed in vacuo and the residue extracted with methylene chloride. Removal of the methylene chloride in vacuo gave the product as an oil (87%).

Example 8

Cis phenylmethyl-4-[4-(4-fluorophenyl)-4-hydroxycyclohexyl]-1-piperazine carboxylate A mixture of phenylmethyl 1-piperazine carboxylate (14 mmole), 4-(4-fluorophenyl)-4-hydroxycyclohexanone (14 mmole) and titanium (IV) isopropoxide (16 mmole) was stirred for 2 hr. The mixture was dissolved in ethanol (200 ml) and sodium borohydride (14 mmole) was added. After stirring for 12 hr water (3 ml) was added and the insoluble $TiO_2$ was removed by filtration. The ethanol was removed in vacuo and the residue acidified with 1N HCl to give a solid.

The solid was basified with NaOH and the mixture extracted with methylene chloride. The extracts were dried over $Na_2SO_4$ and the solution concentrated in vacuo. The residue was crystallized from 2-propyl ether to give the product (61%, mp: 111–113° C.). Calc'd for $C_{24}H_{29}FN_2O_3$: C, 69.89%; H, 7.09%; N. 6.80%. Found: C, 69.82%; H, 7.09%; N, 6.70%.

Example 9

Cis 1-(4-fluorophenyl)-4-(1-piperazinyl) cyclohexanol

A mixture of cis phenylmethyl-4-[4-(4-fluorophenyl)-4-hydroxycyclohexyl]-1-piperazine carboxylate (3.0 g, 7.3 mmole) and 10% palladium on carbon (0.3 g) in 50 ml ethanol was shaken with hydrogen for 5 hr. The catalyst was removed, the solution concentrated in vacuo, and the residue recrystallized from 2-propanol to give the product (85%, mp: 188–190° C.). Calc'd for $C_{20}H_{24}FN_4O.0.28C_5H_{10}O_2$: C, 68.09%; H, 8.48%; N, 9.13%. Found: C, 67.76%; H, 8.12%; N, 9.54%.

Example 10

Cis and trans 1,1-dimethylethyl-4-[4-(4-fluorophenyl)-1-cyclohexyl]-1-piperazine carboxylate These compounds were prepared from 4-(4-fluorophenyl)-cyclohexanone (43 mmole) and 1,1-dimethylethyl 1-piperazine carboxylate (43 mmole) by the procedure described in Example 8. The crude product was mixed with 1N HCl to give the insoluble trans isomer which was then converted to the free base (47%, mp:89–91° C.). Calc'd for $C_{21}H_{31}FN_2O_2$: C, 69.59%; H, 8.63%; N, 7.73%. Found: C, 69.84%; H, 8.43%; N, 7.74%.

Purification of the mother liquor from above on silica gel eluting with methanol-methylene chloride (1:99) gave the cis isomer (8%, mp: 75–77° C.). Calc'd for $C_{21}H_{31}FN_2O_2.0.1C_6H_{14}$: C, 69.91%; H, 8.81%; N, 7.55%. Found: C, 70.10%; H, 8.72%; N, 7.24%.

Example 11

Trans 1-[4-(4-fluorophenyl)-1-cyclohexyl]piperazine

This compound was prepared from trans 1,1-dimethylethyl 4-[4-(4-fluorophenyl)-1-cyclohexyl]-1-piperazine carboxylate (1.7 mmole) by treatment with TFA (as described in Example 22) to give the product as the difumarate [95%, mp: 210° C.(dec)]. Calc'd for $C_{16}H_{23}FN_2.2C_4H_4O_4.0.25H_2O$: C, 57.77%; H, 6.39%; N, 5.61%. Found: C, 57.69%; H, 6.23%; N, 5.60%.

Example 12

Cis 1-[4-(4-fluorophenyl)-1-cyclohexyl]piperazine

This compound was prepared from cis 1,1-dimethylethyl 4-[4-(4-fluorophenyl)-1-cyclohexyl]-1-piperazine carboxylate (1.4 mmole) by the method described in Example 11 to give the product as the difumarate [81%, mp: 232° C.(dec)]. Calc'd for $C_{16}H_{23}FN_2.2C_4H_4O_4.0.25H_2O$: C, 57.77%; H, 6.39%; N, 5.61%. Found: C, 57.79%; H, 6.42%; N, 5.51%.

Example 13

Cis and trans 4-[4-(phenylmethyl)-1-piperazinyl]-1-[4-(trifluoromethyl)phenyl]cyclohexanol To a mixture of magnesium (0.48 g, 20 mmole) in 50 ml dry tetrahydrofuran containing a crystal of iodine, 4-bromobenzo-trifluoride (4.5 g, 20 mmole) was added, and the mixture warmed until the color faded. An exothermic reaction began and the mixture was stirred with cooling until the magnesium dissolved. The solution was cooled to −60° C., and 4-[4-(phenylmethyl)-1-piperazinyl]cyclohexanone (30 g, 11 mmole) was added. After stirring for 1 hr with cooling, the mixture was allowed to warm to room temperature and stirred for 3 hr. The mixture was quenched with saturated ammonium chloride solution. The aqueous layer was separated and extracted with ether. The combined organic solutions were washed with 1N HCl. The acid washes were basified with $K_2CO_3$ and the basic mixture extracted with ether. The ether extracts were dried over $Na_2SO_4$ and concentrated in vacuo. The residue was triturated with isopropyl ether to give the cis isomer (24%, mp: 156–157° C.). Calc'd for $C_{24}H_{29}F_3N_2O$: C, 68.88%; H, 6.99%; N, 6.70%. Found: C, 69.05%; H, 7.06%; N, 6.75%.

Chromatographic purification of the mother liquor on silica eluting with 2% methanol in 1:1 ethyl acetate-hexane gave the trans isomer (17%, mp: 123–124° C.). Calc'd for $C_{24}H_{29}F_3N_2O$: C, 68.88%; H, 6.99%; N, 6.70%. Found: C, 68.54%; H, 6.54%; N, 6.55%.

Example 14

Cis and trans 1-(4-fluoro-1-naphthalenyl)-4-[4-(phenylmethyl)-1-piperazinyl]cyclohexanol These compounds were prepared from 4-fluoro-1-bromonaphthalene (12 mmole) and 4-[4-(phenylmethyl)-1-piperazinyl]cyclohexanone (10 mmole) by the method described in Example 13 which after separation as described gave the cis isomer (12%, mp: 205–207° C.). Calc'd for $C_{27}H_{31}FN_2O.0.4H_2O$: C, 76.17%; H, 7.53%; N, 6.59%; $H_2O$, 1.69%. Found: C, 76.03%; H, 7.36%; N, 6.68%; $H_2O$, 0.94%

The trans isomer was isolated as the dihydrochloride (12%, mp:290–292° C. dec). Calc'd for $C_{27}H_{31}FN_2O.2HCl.H_2O.0.4C_4H_6O$: C, 63.26%; H, 7.15%; N, 5.31%. Found: C, 63.28%; H, 6.93%; N, 4.98%.

Example 15

Cis and trans 1-(1,3-benzodioxol-5-yl)-4-[4-(phenylmethyl)-1-piperazinyl]cyclohexanol These compounds were prepared from 4-bromo-1,2-methylenedioxybenzene (15 mmole) and 4-[4-(phenylmethyl)-1-piperazinyl]cyclohexanone (10 mmole) by the method described in Example 13 which after separation gave the cis isomer (20%, mp: 167–168° C.). Calc'd for $C_{24}H_{30}N_2O_3$: C, 73.07%; H, 7.69%; N, 7.11%. Found: C, 73.05%; H, 7.69%; N, 7.09%.

The trans isomer was isolated as the difumarate salt (6%, mp: 251–252° C.dec). Calc'd for $C_{24}H_{30}N_2O_3.C_4H_4O_4$: C, 61.33%; H, 6.11%; N, 4.47%. Found: C, 61.09%; H, 5.61%; N, 4.47%.

Example 16

Cis and trans 1-(4-methoxyphenyl)-4-[4-(phenylmethyl)-1-piperazinyl]cyclohexanol These compounds were prepared from 4-bromoanisole (15 mmole) and 4-[4-(phenylmethyl)-1-piperazinyl] cyclohexanone (10 mmole) by the method described in Example 13 which after separation gave the cis isomer (50%, mp: 179–180° C.). Calc'd for $C_{24}H_{32}N_2O_2$: C, 75.76%; H, 8.48%; N, 7.37%. Found: C, 75.79%; H, 8.65%; N, 7.35%.

The trans isomer was isolated as the free base (9%, mp:154–156° C.). Calc'd for $C_{24}H_{32}N_2O_2 \cdot 0.2CH_2Cl_2$: C, 73.12%; H, 8.22%; N, 7.05%. Found: C, 72.96%; H, 8.53%; N, 7.02%.

Example 17

Cis and trans-1-(phenylmethyl)-4-[4-(phenylmethyl)-1-piperazinyl]cyclohexanol

These compounds were prepared from benzylmagnesium chloride (30 mmole) and 4-[4-(phenylmethyl)-1-piperazinyl]-cyclohexanone (20 mmole) by the method described in Example 13 which after separation gave the cis isomer (6%, mp: 85–87° C.). Calc'd for $C_{24}H_{32}N_2O$: C, 79.08%; H, 8.85%; N, 7.69. Found: C, 78.87%; H, 8.60%; N, 7.64%.

The trans isomer was isolated as the difumarate (6%, mp: 236–238° C.). Calc'd for $C_{24}H_{32}N_2O \cdot C_4H_4O_4 \cdot 0.2H_2O$: C, 64.03%; H, 6.79%; N, 4.67%. Found: C, 63.85%; H, 6.70%; N, 4.67%.

Example 18

Cis and trans 4-{4-[(fluorophenyl)methyl]-1-piperazinyl]-1-(4-fluorophenyl)cyclohexanol These compounds were prepared from 4-fluorophenylmagnesium bromide (25 mmole) and 4-{4-[(4-fluorophenyl)-methyl]-1-piperazinyl]cyclohexanone (15 mmole) by the method described in Example 13 which after separation gave the cis isomer (40%, mp: 159–160° C.). Calc'd for $C_{23}H_{28}F_2N_2O$: C, 71.48%; H, 7.31%; N, 7.25%. Found: C, 71.48%; H, 7.22%; N, 7.17%.

The trans isomer was obtained as the free base (17%, mp: 104–107° C.). Found: C, 71.66%; H, 7.39%; N, 7.22%.

Example 19

Cis and trans 4-{4-[(4-fluorophenyl)methyl]-1-piperazinyl]-1-[4(trifluoromethyl)-phenyl]cyclohexanol These compounds were prepared from 4-bromobenzotrifluoride (40 mmole) and 4-{4-[(4-fluorophenyl)methyl]-1-piperazinyl]cyclohexanone (25 mmole) by the method described in Example 13 which after separation gave the cis isomer (34%, mp: 165–166° C.). Calc'd for $C_{24}H_{28}F_4N_2O$: C, 66.05%; H, 6.47%; N, 6.42%. Found: C, 65.79%; H, 6.63%; N, 6.39%.

The trans isomer was obtained as the free base (9%, mp: 126–127° C.). Found: H, 65.93%; H, 6.85%; N, 6.35%.

Example 20

Cis and trans 1-(2-benzothiazolyl)-4-[4-(phenylmethyl)-1-piperazinyl]cyclohexanol To a solution of benzothiazole (20 mmole) in THF at 0° C., was added butyl lithium (20 mmole). The solution was cooled to −78° C. and 4-[4-(phenylmethyl)-1-piperazine] cyclohexanone (20 mmole) was added. The solution was allowed to stir for 3 hr as it was allowed to warm to 25° C. The solution was quenched with water and the solvent removed in vacuo. The residue was dissolved in methylene chloride and the solution washed with brine. The organic layer was dried with $Na_2SO_4$ and the solution concentrated in vacuo. The residue was crystallized from methylene chloride-ether to give the cis isomer (4%, mp: 173–176° C.).

Calc'd for $C_{24}H_{29}N_2OS$: C, 70.73%; H, 7.18%; 10.32%. Found: C, 70.63%; H, 7.15%; 10.24%.

The trans isomer was isolated from the mother liquors by chromatography on alumina eluting first with ethyl acetate-hexane followed by ethyl acetate-methanol. The trans product was purified as the difumarate salt (4%, mp: 234–235° C.) Calc'd for $C_{24}H_{29}N_2OS \cdot C_4H_4O_4$: C, 60.09%; H, 5.84%; N, 6.57%. Found: C, 59.83%; H, 5.77%; N, 6.55%.

Example 21

Cis 1,1-dimethylethyl-4-[4-(4-fluorophenyl)-4-hydroxycyclohexyl]-1-piperazine carboxylate A mixture of 1,1-dimethylethyl 1-piperazine carboxylate (24 mmole) and 4-(4-fluorophenyl)-4-hydroxycyclohexanone (24 mmole) as reacted by the method of Example 8 to give the product (79%, mp: 162–164° C.). Calc'd for $C_{21}H_{31}FN_2O_3 \cdot 0.1H_2O$: C, 66.33%; H, 8.28%; N, 7.37%; $H_2O$, 0.47%. Found: C, 66.14%; H, 8.12%; N, 7.26%; $H_2O$, 0.45%.

Example 22

1-[4-(4-Fluorophenyl)-3-cyclohexen-1-yl]piperazine

Trifluoroacetic acid (10 ml) was added to cis 1,1-dimethylethyl-4[4-(4-fluorophenyl)-4-hydroxycyclohexyl]-1-piperazine carboxylate (1.9 g, 5 mmole) with immediate evolution of gas. After stirring for 1 hr, the solution was concentrated in vacuo and the residue suspended in water. The mixture was basified with $K_2CO_3$ and extracted with methylene chloride. The extracts were dried and concentrated in vacuo to furnish the crude product. The material was acidified with fumaric acid in ethyl acetate to give the difumarate (85%, mp: 212–213° C.). Calc'd for $C_{16}H_{21}FN_2 \cdot 2C_4H_4O_4$: C, 58.54%; H, 5.94%; N, 5.69%. Found: C, 58.40%; H, 5.83%; N, 5.61%.

Example 23

8-(1,3-Benzodioxol-5-yl)-1,4-dioxaspiro[4.5]decan-8-ol

A solution of 1,4-cyclohexanedione monoethylene ketal (25 g, 160 mmole) in dry THF (250 ml) was reacted with the Grignard reagent prepared from 5-bromo-1,3-benzodioxole (40 g, 200 mmole) and magnesium (4.8 g, 200 mmole) as described in example 3 to give the product (52%, mp: 95–96° C.). Calc'd for $C_{15}H_{18}O_5$: C, 64.74%; H, 6.52%. Found: C, 64.41%; H, 6.41%.

Example 24

8-(3,4-Difluorophenyl)-1,4-dioxaspiro[4.5]decan-8-ol

A solution of 1,4-cyclohexanedione monoethylene ketal (15.6 g, 100 mmole) in dry THF (250 ml) was reacted with a solution of the Grignard reagent prepared from 1-bromo-3,4-difluorobenzene (19 g, 100 mmole) and magnesium (2.4 g, 100 mmole) in dry THF at −60° C. as described in example 3 to give the product (38%, mp: 118–120° C.). Calc'd for $C_{14}H_{16}F_2O_3$: C, 62.22%; H,5.97%. Found: C, 61.97%; H, 6.35%.

Example 25

4-(1,3-Benzodioxol-5-yl)-4-hydroxycyclohexanone

A solution of 8-(1,3-benzodioxol-5-yl)-1,4-dioxaspiro-[4.5]decan-8-ol (5.0 g, 1.8 mmole) in acetone (75 ml) and concentrated HCl (1 ml) was stirred for 2 hr. The insoluble product was collected and dried (96%, mp: 162–164° C.). Calc'd for $C_{13}H_{14}O_4$: C, 66.66%; H, 6.03%. Found: C, 65.69%; H, 5.95%.

Example 26

4-(3,4-Difluorophenyl)-4-hydroxycyclohexanone

A solution of 8-(3,4-difluorophenyl)-1,4-dioxaspiro[4.5]decan-8-ol (3 mmole) in acetone (100 ml) and concentrated HCl (1 ml) was reacted as described in example 25 to give the product (48%, mp: 84–85° C.). Calc'd for $C_{12}H_{12}F_2O_2$: C, 63.72%; H, 5.35%. Found: C, 62.72%; H, 5.24%.

Example 27

Cis phenylmethyl-4-[4-(1,3-benzodioxol-5-yl)-4-hydroxy-1-cyclohexyl]-1-piperazine carboxylate A mixture of titanium (IV) isopropoxide (17 ml, 50 mmole), 4-(1,3-benzodioxol-5-yl)-4-hydroxycyclohexanone (6.0 g, 25.7 mmole), carbobenzyloxypiperazine (5.6 g, 25.7 mmole) and sodium borohydride (1.0 g, 25 mmole) was reacted as described in example 1 to give the product (88%, mp: 122–124° C.). Calc'd for $C_{25}H_{30}N_2O_5 \cdot 0.5H_2O$: C, 67.10%; H, 6.99%; N, 6.26%. Found: C, 67.18%; H, 6.80%; N, 6.26%.

Example 28

Cis 1-(1,3-benzodioxol-5-yl)-4-(1-piperazinyl)cyclohexanol

A mixture of cis phenylmethyl 4-[4-(1,3-benzodioxol-5-yl)-4-hydroxy-1-cyclohexyl]-1-piperazine carboxylate (0.44 g, 1 mmole) and 10% palladium on charcoal (0.1 g) in ethanol was hydrogenated for 1 hr and the catalyst removed. The solvent was removed in vacuo and the residue crystallized from 2-propyl ether to give the product (97%, mp: 198–199° C.). Calc'd for $C_{17}H_{24}N_2O_3 \cdot 0.5H_2O$: C, 65.16%; H, 8.05%; N, 8.94%. Found: C, 65.27%; H, 7.69%; N, 8.83%.

Example 29

1-[4-(1,3-Benzodioxol-5-yl)-3-cyclohexen-1-yl]piperazine

A solution of cis 1-(1,3-benzodioxol-5-yl)-4-(1-piperazinyl)cyclohexanol (0.25 g, 0.8 mmole) in trifluoroacetic acid (5 ml) was reacted as described in example 22 to give the product (100%, mp: 130–131° C.). Calc'd for $C_{17}H_{22}N_2O_2 \cdot 0.2H_2O$: C, 70.42%; H, 7.79%; N, 9.66%. Found: C, 70.78%; H, 7.66%; N, 9.66%.

Example 30

Cis 1-(1,4-benzodiox-6-yl)-4-[4-(phenylmethyl)piperazinyl]-cyclohexanol

The Grignard reagent prepared from 6-bromo-1,4-benzodioxane (5 g, 23 mmole), magnesium (0.56 g, 23 mmole) and 4-[(4-phenylmethyl)-1-piperazinyl]cyclohexanone (3 g, 11 mmole) were reacted as described in example 3 to give the product (73%, mp: 178–179° C.). Calc'd for $C_{25}H_{32}N_2O_3 \cdot 0.05H_2O$: C, 73.34%; H, 7.91%; N, 6.85%. Found: C, 73.04%; H, 7.91%; N, 7.25%.

Example 31

Cis 1-(1,3-benzodioxol-5-yl)-4-{4-[4-(3-methoxyphenyl)methyl]-1-piperidinyl}cyclohexanol Titanium(IV) isopropoxide (2.5 ml, 7.6 mmole), 4-(1,3-benzodioxol-5-yl)-4-hydroxycyclohexanone (1.4 g, 5.8 mmole), 4-(3-methoxybenzyl)piperazine (1.2 g, 5.8 mmole) and sodium borohydride (0.23 g, 5.8 mmole) were reacted as described in example 1 above to give the product, (8.3%, mp: 164–165° C.). Calc'd for $C_{26}H_{33}NO_4$: C, 73.73%; H, 7.85%; N, 3.31%. Found: C, 73.45%; H, 7.88%; N, 3.20%.

Example 32

Cis 1-(1,3-benzodioxol-5-yl)-4-[4-[4-(2,5-difluorophenyl)-methyl]-1-piperidinyl]cyclohexanol Titanium (IV) isopropoxide (1.1 ml, 3.3 mmole), 4-(1,3-benzodioxol-5-yl)-4-hydroxycyclohexanone (0.7 g, 3 mmole), 4-(2,5-difluorobenzyl)piperazine (0.63 g, 3 mmole), and sodium borohydride (0.12 g, 3 mmole) were reacted as described in example 1 above to give the product (38%, mp: 167–168° C.). Calc'd for $C_{25}H_{29}F_2NO_3$: C, 69.91%; H, 6.81%; N, 3.26%. Found: C, 69.82%; H, 6.71%; N, 3.24%.

Example 33

Cis 1-(1,3-benzodioxol-5-yl)-4-{4-[4-(2-fluorophenyl)methyl]-1-piperidinyl]cyclohexanol Titanium(IV) isopropoxide (3.7 ml, 11 mmole), 4-(1,3-benzodioxol-5-yl)-4-hydroxycyclohexanone (2.3 g, 10 mmole), 4-(2-fluorobenzyl)piperazine (1.9 g, 10 mmole), and sodium borohydride (0.4 g, 10 mmole) were reacted as described in example 1 above to give the product (10%. mp: 180–181° C.). Calc'd for $C_{25}H_{30}FNO_3$: C, 72.97%; H, 7.35%; N, 3.41%. Found: C, 72.90%; H, 7.36%; N, 3.36%.

Example 34

Cis 1-(3,4-difluorophenyl)-4-{4-[4-(2,5-difluorophenyl)-methyl]-1-piperidinyl]cyclohexanol Titanium (IV) isopropoxide (1.1 ml, 3.3 mmole), 4-(3,4-difluorophenyl)-4-hydroxycyclohexanone (0.68 g, 3 mmole), 4-(2,5-difluorobenzyl)piperazine (0.63 g, 3 mmole), and sodium borohydride (0.12 g, 3 mmole) were reacted as described in example 1 above to give the product (69%, mp: 158–159° C.). Calc'd for $C_{24}H_{27}F_4NO$: C, 68.40%; H, 6.46%; N, 3.33%. Found: C, 68.25%; H, 6.71%; N, 3.25%.

B. Preparation of Compounds of Formula I

Example 35

1-[4-(4-Fluorophenyl)-3-cyclohexen-1-yl]-4-(phenylmethyl)-piperazine

A mixture of cis and trans 1-(4-fluorophenyl)-4-[4-(phenylmethyl)-1-piperazinyl]cyclohexanol (2.4 g, 6.5 mmole) and thionyl chloride (2.2 g, 18.6 mmole) in 100 ml methylene chloride was stirred for 18 hr and concentrated in vacuo to give a solid. The crude product was recrystallized from 2-propanol to give the product as the dihydrochloride hydrate [87%, mp: 283–285° C.(dec)]. Calc'd for $C_{23}H_{27}FN_2 \cdot 2HCl \cdot 0.5H_2O$: C, 63.89%; H, 7.00%; N, 6.48%; $H_2O$, 2.08%. Found: C, 63.57%; H, 7.00%; N, 6.27%; $H_2O$, 1.51%.

Example 36

1-[4-(4-Fluoro-1-naphthalenyl)-3-cyclohexen-1-yl]-4-(phenylmethyl)piperazine

To a suspension of 1-(4-fluoro-1-naphthalenyl)-4-[4-(phenylmethyl)-4-piperazinyl]cyclohexanol (1.8 g, 4.3 mmole) in trifluoroacetic anhydride (10 ml), was added trifluoroacetic acid (30 ml) and the solution heated at reflux for 18 hr. The solution was diluted with water and basified with potassium carbonate. The basic mixture was extracted with ether and the extracts dried over sodium sulfate. The solution was acidified with ethanolic hydrogen chloride to give a solid. Recrystallization from methanol-water gave the product (79%, dp: 285–293° C.). Calcd for $C_{27}H_{29}FN_2 \cdot 2HCl$: C, 68.50%; H, 6.60%; N, 5.92%. Found: C, 68.54%; H, 6.59%; N, 5.92%.

Example 37

1-[4-(1,3-Benzodioxol-5-yl)-3-cyclohexen-1-yl]-4-(phenylmnethyl) piperazine

A solution of 1-(1,3-benzodioxol-5-yl)4-[4-(phenylmethyl)-1-piperazinyl]cyclohexanol (2.0 g, 5.08 mmole) in pyridine (40 ml) and phosphorous oxychloride (10 ml) was stirred for 18 hr and heated at 80–100° C. for 2 hr. The cooled mixture was carefully added to ice-water and the insolubles collected. The damp solid was suspended in water and the mixture basified with potassium hydroxide. The basic mixture was extracted with ether. The extracts were dried over sodium sulfate and the solution concentrated in vacuo. The solid residue was recrystallized from 2-propanol to give the product (55%, mp: 151–152° C.). Calc'd for $C_{24}H_{28}N_2O_2$: C, 76.57%; H, 7.50%; N, 7.45%. Found: C, 76.57%; H, 7.45%; N, 7.42%.

Example 38

1-[4-(2-Benzothiazolyl)-3-cyclohexen-1-yl]-4-(phenylmethyl)piperazine

This compound was prepared from 1-(2-benzothiazolyl)-4-[4-(phenylmethyl)1-piperazinyl]cyclohexanol (8 mmole) in a manner as described in Example 36 above to yield the crude product which was recrystallized from ethyl acetate-hexane (46%, mp: 132–134° C.). Calc'd for $C_{24}H_{27}N_3S$: C, 74.00%; H, 6.99%; N, 10.79%. Found: C, 73.60%; H, 6.95%; N, 10.72%.

Example 39

1-[4-(4-Methoxyphenyl)-3-cyclohexen-1-yl]-4-(phenylmethyl)piperazine

This compound was prepared from 1-(4-methoxyphenyl)-4-[4-(phenylmethyl)-1-piperazinyl]cyclohexanol (8.9 mmole) in a manner described in Example 37 above to yield a solid which was recrystallized from ethyl ether to give the product (87%, mp: 126–128° C.). Calc'd for $C_{24}H_{30}N_2O$: C, 79.52%; H, 8.35%; N, 7.73%. Found: C, 79.36%; H, 8.33%; N, 7.72%.

Example 40

1-(Phenylmethyl)-4-[4-[4-(trifluoromethyl)phenyl]-3-cyclohexen-1-yl]piperazine

This compound was prepared from 4-[4-(phenylmethyl)-1-piperazinyl]-1-[4-(trifluoromethyl)phenyl]cyclohexanol (3.1 mmole) in a manner described for Example 37 above to give a solid which was recrystallized from hexane to give the product (36%, mp: 115–116° C.). Calc'd for $C_{24}H_{27}F_3N_2$: C, 71.98%; H, 6.80%; N, 7.00%. Found: C, 71.95%; H, 6.79%; N, 6.97%.

Example 41

1-[4-(4-Fluorophenyl)-3-cyclohexen-1-yl]-4-[(4-fluorophenyl)methyl]piperazine

This compound was prepared from 1-(4-fluorophenyl)-4-{4-[(4-fluorophenyl)-methyl]-1-piperazinyl]cyclohexanol (2.8 mmole) in a manner described for Example 37 above to give a solid which was recrystallized from hexane to give the product (50%, mp: 109–110° C.). Calc'd for $C_{23}H_{26}F_2N_2$: C, 74.98%; H, 7.12%; N, 7.51%. Found: C, 75.11%; H, 7.08%; N, 7.56%.

Example 42

1-[(4-Fluorophenyl)methyl]-4-[4-[4-(trifluoromethyl)phenyl]-3-cyclohexen-1-yl]piperazine This compound was prepared from 4-[4-[(4-fluorophenyl)-methyl]-1-piperazinyl]-1-[4-(trifluoromethyl)-phenyl]cyclohexanol (4.6 mmole) in a manner described for Example 37 above to provide a solid which was recrystallized from petroleum ether to give the product (70%, mp: 108–109° C.). Calc'd for $C_{24}H_{26}F_4N_2$: C, 68.88%; H, 6.26%; N, 6.69%. Found: C, 68.98%; H, 6.42%; N, 6.65%.

Example 43

1-(Phenylmethyl)-4-[4-(phenylmethyl)-3-cyclohexen-1-yl]piperazine

This compound was prepared from 1-(phenylmethyl)-4-[4-(phenylmethyl)-1-piperazinyl]cyclohexanol (5.5 mmole) in a manner described for Example 37 above to give a solid which was converted to the fumarate salt and recrystallized from methanol-ethyl acetate (84%, mp: 241–243° C.). Calc'd for $C_{24}H_{30}N_2 \cdot 2C_4H_4O_4$: C, 66.43%; H, 6.62%; N, 4.85%. Found: C, 66.48%; H, 6.50%; N, 4.88%.

Example 44

1-[4-(4-Fluorophenyl)-3-cyclohexen-1-yl]-4-(2-thienylmethyl)piperazine

A solution of 2-thiophenecarboxaldehyde (4 mmole), 1-[4-(4-fluorophenyl)-3-cyclohexen-1-yl]piperazine (4 mmole), and sodium cyanoborohydride (4 mmole) was heated at reflux for 6 hr. The solution was acidified with HCl. After stirring for 1 hr the ethanol was removed in vacuo. The residue was basified with NaOH and the mixture extracted with methylene chloride. The solution was dried over $Na_2SO_4$ and the solution concentrated in vacuo. The residue was dissolved in ethanol and acidified with HCl to give the product as the dihydrochloride [47%, mp: 287–280° C.(dec)]. Calc'd for $C_{21}H_{25}FN_2S \cdot 2HCl \cdot 0.5H_2O$: C, 57.53%; H, 6.44%; N, 6.39%; $H_2O$, 2.05%. Found: C, 57.63%; H, 6.40%; N, 6.51%; $H_2O$, 1.10%.

Example 45

2{{4-[4-(4-Fluorophenyl)-3-cyclohexen-1-yl]-1-piperazinyl]methyl]quinoline

A mixture of 2-chloromethylquinoline (4.7 mmole), and 1-[4-(4-fluorophenyl)-3-cyclohexen-1-yl]piperazine (4.7 mmole) and excess powdered $K_2CO_3$ was heated at reflux for 18 hr. The insolubles were removed by filtration, the solution concentrated in vacuo, and the residue crystallized from hexane to give the product (53%, mp: 111–114° C.). Calc'd for $C_{26}H_{28}FN3$: C, 77.78%; H, 7.03%; N, 10.47%. Found: C, 77.61; H, 6.91%; N, 10.72%.

Example 46

1-[4-(4-Fluorophenyl)-3-cyclohexen-1-yl]-4-(4-pyridinylmethyl)piperazine

A mixture of 4-chloromethylpyridine (3.8 mmole) and 1-[4-(4-fluorophenyl)-3-cyclohexen-1-yl]piperazine were reacted by the method of Example 45 to give the product as the difumarate [67%, mp: 192–194° C.(dec)]. Calc'd for $C_{24}H_{26}FN_3 \cdot 2C_4H_4O_4$: C, 61.75%; H, 5.88%; N, 7.20%. Found: C, 61.66%; H, 5.87%; N, 7.17%.

Example 47

1-[4-(4-Fluorophenyl)-3-cyclohexen-1-yl]-4-(phenylmethyl)piperidine

4-Fluorophenyl magnesium bromide (10 mmole) and 4-[4-(phenylmethyl)-1-piperidinyl]cyclohexanone (7.38 mmole) were reacted by the method described in Example 13 to give the intermediate mixture of cis and trans alcohols. This crude mixture was then dehydrated using $SOCl_2$ in $CH_2Cl_2$ by the method described in Example 35 to give the crude product which was purified by chromatography on silica gel using ethyl acetate as the eluent. The pure product was converted the HCl salt in acetone using 12N HCl (23.3% overall, mp: 214–217° C.). Calc'd for $C_{24}H_{28}NF \cdot HCl \cdot 0.25H_2O$: C, 73.83%; H, 7.62%; N, 3.59%. Found: C, 73.85%; H, 7.61%; N, 3.56%.

Example 48

5-Methoxy-3-[4-[4-(phenylmethyl)-1-piperazinyl]-1-cyclohexen-1-yl]-1H-indole A solution of 5-methoxyindole (3.68 mmole), 4-[4-(phenylmethyl)-1-piperazinyl]cyclohexanone (3.68 mmole), and pyrrolidine (0.25 ml) in ethanol (10 ml) was heated at reflux for 96 hr. The solution was concentrated in vacuo and the residue purified by chromatography on silica eluting with ethyl acetate in hexane to give the product which was converted to the fumarate salt in ethyl acetate (38.4%, mp: 199–200° C.). Calc'd for $C_{26}H_{31}N_3O \cdot 2C_2H_2O_2$: C, 64.45%; H, 6.21%; N, 6.64%. Found: C, 64.42%; H, 6.21%; N, 6.61%.

Example 49

5-Fluoro-3-{4-[4-(phenylmethyl)-1-piperazinyl]-1-cyclohexen-1-yl]-1H-indole This compound was prepared from 5-fluoroindole and 4-[4-(phenylmethyl)-1-piperazinyl]cyclohexanone in a manner described for Example 48 above to give the product as the fumarate salt (76%, mp: 202–205° C.). Calc'd for $C_{25}H_{28}FN_3 \cdot C_4H_4O_4$: C, 69.04%; H, 6.20%; N, 8.33%. Found: C, 68.81%; H, 6.34%; N, 8.25%.

Example 50

5-Chloro-3-{4-[4-(phenylmethyl)-1-piperazinyl]-1-cyclohexen-1-yl]-1H-indole This compound was prepared from 5-chloroindole and 4-[4-(phenylmethyl)-1-piperazinyl]cyclohexanone in a manner described for Example 48 above to give the product as the fumarate salt (56%, mp: 191–195° C.). Calc'd for $C_{25}H_{28}ClN_3 \cdot 2C_4H_4O_4$: C, 62.12%; H, 5.69%; N, 6.59%. Found: C, 62.01%; 5.50%; N, 6.52%.

Example 51

5-Fluoro-3-{4-[4-(phenylmethyl)-1-piperidinyl]-1-cyclohexen-1-yl]-1H-indole This compound was prepared from 5-fluoroindole and 4-[4-(phenylmethyl)-1-piperidinyl]cyclohexanone by the method described in Example 48 to give the product (87.1%, mp:72–74° C.). Calc'd for $C_{26}H_{29}FN_2 \cdot 0.15C_2H_5OH$: C, 79.83%; H, 7.72%; N, 7.04%. Found: C, 79.89%; H, 7.63%; N, 7.09%.

Example 52

1-[4-(1,3-Benzodioxol-5-yl)-3-cyclohexen-1-yl]-4-[(3-methoxyphenyl)methyl]piperidine Phosphorous oxychloride (1 ml), cis-1-(1,3-benzodioxol-5-yl)-4-{[4-(3-methoxy-phenyl)methyl]piperidinyl] cyclohexanol (0.3 g, 0.7 mmole) and pyridine (3 ml) were reacted as described in example 37 to give the product which was isolated as the fumarate (71%, mp: 154–157° C.). Calc'd for $C_{26}H_{31}NO_3 \cdot C_4H_4O_4 \cdot H_2O$: C, 66.77%; H, 6.91%; N, 2.60%. Found: C, 66.78%; H, 6.87%; N, 2.88%.

Example 53

1-[4-(1,3-Benzodioxol-5-yl)-3-cyclohexen-1-yl]-4-[(2-fluorophenyl)methyl]piperidine Phosphorous oxychloride (1 ml), cis-1-(1,3-benzodioxol-5-yl)-4-{[4-(2-fluoro-phenyl)methyl]piperidinyl] cyclohexanol (0.37 g, 0.9 mmole), and pyridine (4 ml) were reacted as described in example 37 to give the title compound (83%, mp: 118–119° C.). Calc'd for $C_{25}H_{28}FNO_2$: C, 76.31%; H, 7.18%; N, 3.56%. Found: C, 76.59%; H, 7.27%; N, 3.52%.

Example 54

1-[4-(1,3-Benzodioxol-5-yl)-3-cyclohexen-1-yl]-4-[(2,5-difluorophenyl)methyl]piperidine Phosphorous oxychloride (1.5 ml), cis-1-(1,3-benzodioxol-5-yl)-4-{[4-(2,5-difluorophenyl)methyl] piperidinyl]-cyclohexanol (0.37 g, 0.9 mmole), and pyridine (4.5 ml) were reacted as described in example 37 to give the title compound, (100%, mp: 87–88° C.). Calc'd for $C_{25}H_{27}F_2NO_2$: C, 72.98%; H, 6.62%; N, 3.41%. Found: C, 72.57%; H, 6.60%; N, 3.33%.

Example 55

1-[4-(3,4-Difluorophenyl)-3-cyclohexen-1-yl]-4-[(2,5-difluorophenyl)methyl]piperidine Phosphorous oxychloride (1.6 ml), cis-1-(3,4-difluorophenyl)-4-{[4-(2,5-difluoro-phenyl)methyl]-piperidinyl]cyclohexanol (0.95 g, 2.2 mmole) and pyridine (5 ml) were reacted as described in example 37 to give the product which was isolated as the fumarate (91%, mp: 205–206° C.). Calc'd for $C_{24}H_{25}F_4N \cdot C_4H_4O_4$: C, 64.74%; H, 5.63%; N, 2.70%. Found: C, 64.68%; H, 5.63%; N, 2.64%.

Example 56

1-[4-(1,4-Benzodioxan-6-yl)-3-cyclohexen-1-yl]-4-(phenylmethyl)piperazine

Phosphorous oxychloride (2 ml), cis-1-(1,4-benzodioxan-6-yl)-4-[4-(phenylmethyl)-piperazinyl]cyclohexanol (1 g, 2.4 mmole), and pyridine (8 ml) were reacted as as described in example 37 to give the title compound (58%, mp: 132–133° C.). Calc'd for $C_{25}H_{30}N_2O_2 \cdot 0.5H_2O$: C, 75.16; H, 7.83; N, 7.02. Found: C, 74.99; H, 7.66; N, 7.20.

Example 57

1-[4-(1,3-Benzodioxol-5-yl)-3-cyclohexen-1-yl]-4-[(2-chlorophenyl)methyl]piperazine The title compound was prepared from 2-chlorobenzylchloride (0.16 g, 1 mmole), 1-[4-(1,3-benzodioxol-5-yl)-3- cyclohexen-1-yl]piperazine (0.29 g, 1 mmole), and excess powdered K₂CO₃ as described in example 45 to give the product (78%, mp: 115–116° C.). Calc'd for $C_{24}H_{27}ClN_2O_2$: C, 70.14%; H, 6.62%; N, 6.82%. Found: C, 70.25; H, 6.69%; N, 6.83%.

Example 58

1-[4-(1,3-Benzodioxol-5-yl)-3-cyclohexen-1-yl]-4-[(2,5-difluorophenyl)methyl]piperazine The title compound was prepared from 2,5-difluorobenzyl bromide (0.21 g, 1 mmole), and 1-[4-(1,3-benzodioxol-5-yl)-3-cyclohexen-1-yl]piperazine (0.29 g, 1 mmole), and excess powdered K₂CO₃ as described in example 45 to give the product (62%, mp: 108–109° C.). Calc'd for $C_{24}H_{26}F_2N_2O_2$: C, 69.88%; H, 6.35%; N, 6.79%. Found: C, 69.82; H, 6.35%; N, 6.69%.

Example 59

1-[4-(1,3-Benzodioxol-5-yl)-3-cyclohexen-1-yl]-4-[(3-methoxyphenyl)methyl]piperazine The title compound was prepared from 3-methoxybenzyl chloride (0.13 g, 0.8 mmole), 1-[4-(1,3-benzodioxol-5-yl)-3-cyclohexen-1-yl]piperazine (0.23 g, 0.8 mmole), and excess powdered K₂CO₃ as described in example 45 to give the product (45%, mp: 124–124.5° C.). Calc'd for $C_{25}H_{30}N_2O_3$: C, 73.86%; H, 7.44%; N, 6.89%. Found: C, 73.88; H, 7.43%; N, 6.91%.

Example 60

1-[(4-Fluorophenyl)-3-cyclohexen-1-yl]-4-[(3-methoxyphenyl)methyl]piperazine

The title compound was prepared from 3-methoxybenzyl bromide (0.31 g, 2 mmole), 1-[4-(1,3-benzodioxol-5-yl)-3-cyclohexen-1-yl]piperazine (0.52 g, 2 mmole), and excess powdered K₂CO₃ as described in example 37 to give the product (86%, mp: 69–71° C.). Calc'd for $C_{24}H_{29}FN_2O$: C, 75.76%; H, 7.69%; N, 7.37%. Found: C, 75.62%; H, 7.61%; N, 7.10%.

Example 61

1-[4-(1,3-Benzodioxol-5-yl)-3-cyclohexen-1-yl]-4-[(2,5-diiodophenyl)methyl]piperazine The title compound was prepared from 1-[4-(1,3-benzodioxol-5-yl)-3-cyclohexen-1-yl]piperazine (0.25 g, 0.87 mmole) and 2,5-diiodobenzyl chloride (0.33 g, 0.87 mmole) by the method described in example 45 to give the product (82%, mp: 174–175° C.). Calc'd for $C_{24}H_{26}I_2N_2O_2$: C, 45.89%; H, 4.18%; N, 4.46%. Found: C, 45.58%; H, 4.13%; N, 4.35%.

Example 62

Cis and trans 1-[4-(4-fluoro-1-naphthalenyl)-1-cyclohexyl]-4-(phenylmethyl)piperazine A mixture of platinum oxide (0.1 g) and 1-[4-(4-fluoro-1-naphthalenyl)-3-cyclohexen-1-yl]-4-(phenylmethyl)piperazine (1.1 g, 2.7 mmole) was hydrogenated for 13 hr in 20 ml acetic acid. The catalyst was removed and the solution concentrated in vacuo. The residue was suspended in water and the mixture basified with potassium carbonate. The mixture was extracted with ether, the extracts were dried over sodium sulfate and the solution concentrated in vacuo. The residue was purified by chromatography on silica gel eluting with 2-propanol-ethyl acetate-hexane (3:10:87). Fractions containing the less polar material were concentrated in vacuo to give the cis isomer (25%, mp: 130–132° C.). Calc'd for $C_{27}H_{31}FN_2 \cdot 0.1H_2O$: C, 80.21%; H, 7.78%; N, 6.93%. Found: C, 80.12%; H, 7.80%; N, 6.89%.

The trans isomer was obtained upon concentration of fractions containing the more polar material (20%, mp: 90–93° C.). Calc'd for $C_{27}H_{31}FN_2 \cdot 0.1H_2O$: C, 80.21%; H, 7.78%; N, 6.93%. Found: C, 80.06%; H, 7.82%, N, 6.87%.

Example 63

Trans 1-[4-(4-fluorophenyl)-1-cyclohexyl]-4-(phenylmethyl)piperazine

A mixture of 4-(4-fluorophenyl)cyclohexanone (7.8 mmole) and 1-(phenylmethyl)piperazine (7.8 mmole) were reacted as described in Example 8. The crude isomer mixture was purified as described in Example 62. Concentration of the fractions containing the more polar isomer gave the trans product (22%, mp: 106–106° C.). Calc'd for $C_{23}H_{29}FN_2$: C, 78.38%; H, 8.30%; N, 7.95%. Found: C, 78.02; H, 8.20%; N, 7.90%.

Example 64

Trans 2-{{4-[4-(4-fluorophenyl)-1-cyclohexyl]-1-piperazinyl}methyl}quinoline

This compound was prepared from trans 1-[4-(4-fluorophenyl)-1-cyclohexyl]piperazine (2.4 mmole) and 2-chloromethylquinoline hydrochloride (2.4 mmole) by the method described in Example 45 to give the product (82%, mp 160–162° C.). Calc'd for $C_{26}H_{30}FN_3 \cdot 0.2H_2O$: C, 76.70%; H, 7.53%; N, 10.32% Found: C, 76.68%; H, 7.49%; N, 10.32%.

Example 65

Trans 1-[4-(4-fluorophenyl)-1-cyclohexyl]-4-[(3-methoxyphenyl)methyl]piperazine

The title compound was prepared from trans 1-[4-(4-fluorophenyl)-1-cyclohexyl]piperazine (0.39 g, 1.5 mmole) and 3-methoxybenzyl chloride (0.22 g, 1.5 mmole) by the method described in example 45 to give the product (61%, mp: 84–85° C.). Calc'd for $C_{24}H_{31}FN_2O$: C, 75.36%; H, 8.17%; N, 7.33%. Found: C, 75.53%; H, 8.23%; N, 7.30%.

Example 66

Anoxic Nitrogen Test in Rats

The animals utilized are male Sprague-Dawley rats (200–400 grams) housed four animals per cage in a normal controlled environment with unlimited access to food and water. Usually there are 8 animals per dose, however, 8 animals can be employed to obtain an initial impression of a compound's activity. Animals are parenterally or orally administered the vehicle or test compound 30 minutes before the anoxic insult. The anoxic episode consists of placing up to 8 animals in the sealed test chamber (10" l×10" w×6" h) continuously flushed with pure N2 (4.5 grade) at a flow rate of 5 SCFM for 1 min. Animals are then promptly removed to normal atmosphere and observed for the 2 hour period. Typically, animals become disoriented within 15 sec after which they remain motionless.

Even though the heart is still beating after the $N_2$ exposure, all control animals fail to gasp when removed from the chamber and usually expire within 3 minutes. Drug treated animals, however, still gasp or start gasping after being removed, which is a good indication that the animals will survive the $N_2$ exposure [see Wauquire, A., et al: *Arch. Int. Pharmacodyn.*, 249, 330–334 (1981); Wauquier, A., et al: *Drug Dev. Res.*, 8, 373–380 (1986)]. Results are recorded as:

(Number of animals surviving (2 hr))/(Number of animals tested)×100%

Example 67

Dopamine $D_2$ Binding Assay

Dopamine $D_2$ affinity was determined according to the procedures of Burt, Creese and Snyder [Molecular Pharmacology 12,800 (1976); Science 196, 326 (1977); Science 192, 481 (1976)]. Briefly, male Sprague-Dawley rats (Charles River) were decapitated, brains rapidly removed and chilled in ice-cold 50 mM Hepes/KOH buffer (pH 7.4, 20° C.). The corpus striatum was crudely dissected and frozen on dry ice. Tissue was pooled and stored at –80° C. until use. On the day of assay, tissue was thawed in 20 ml ice-cold Hepes/KOH buffer, and homogenized with a polytron for 15 sec at 18,000 rpm. The homogenate was centrifuged (39,000×g, 10 min, at 4° C.). The supernatant was discarded and the pellet rehomogenized in ice-cold Hepes/KOH buffer and recentrifuged as described previously. The supernatant was again discarded and the pellet resuspended (1:100) in ice-cold Hepes/KOH buffer (pH 7.4, 20° C., containing 120 mM NaCl, 5 mM KCl, 1 mM $MgCl_2$, 0.1% (w/v) ascorbic acid, and 10 μM pargylline, and stored on ice until assay. The binding assay (1 ml total volume) was performed in duplicate and initiated by the addition of 800 μl membrane homogenate to tubes containing 100 μl [$^3$H] Spiperone (0.1 nM final concentration), and 100 μl competitor, buffer, or butaclamol, which was used to define the non-specific binding. The assay was incubated at 37° C. for 15 min, afterwhich the assay was terminated by rapid filtration. Since the reference agent displays an $IC_{50}$ value of approximately 10 nM, compounds which displace 50% of the binding at greater that 1000 nM are termed inactive.

Table 2 shows the biological activities of the compounds made in Examples through 35–65:

TABLE 2

Biological Activities of Compounds of Formula I

| EX. | $D_2$ binding[a,b] | Sigma binding[b] $IC_{50}$ (nM) | Nitrogen Anoxia[b] % Survival (dose) |
|---|---|---|---|
| 35 | "C" | 1.9 | 100% (15 & 20 mg/kg) |
| 36 | "A" | nd | 100% (50 mg/kg) |
| 37 | "B" | 1.9 | 92% (40 mg/kg) |
| 38 | "B" | 3.9 | 100% (80 mg/kg) |
| 39 | "A" | 0.9 | 92% (20 & 30 mg/kg) |
| 40 | "B" | 4.5 | 100% (10 mg/kg) |
| 41 | "A" | 0.6 | 92% (20 mg/kg) |
| 42 | "D" | 6.9 | 100% (20 mg/kg) |
| 43 | "A" | 2.1 | 75% (5 mg/kg) |
| 44 | "A" | nd | 100% (40 mg/kg) |
| 45 | "A" | nd | 83% (20 mg/kg) |
| 46 | "C" | 0.5 | 83% (20 mg/kg) |
| 47 | "A" | 4.0 | 88% (40 mg/kg) |
| 48 | "A" | 6.2 | 88% (40 mg/kg) |
| 49 | "A" | 8.6 | 92% (10 & 60 mg/kg) |
| 50 | "B" | 31.4 | 100% (20 mg/kg) |
| 50 | "B" | 31.4 | 100% (20 mg/kg) |
| 51 | "A" | 11.1 | 67% (20 & 40 mg/kg) |
| 52 | "A" | 7.4 | 38% (10 mg/kg) |
| 53 | "A" | nd | nd |
| 54 | "A" | 3.6 | 38% (10 mg/kg) |
| 55 | "A" | nd | nd |
| 56 | nd | nd | 100% (10 mg/kg) |
| 57 | "A" | nd | 25% (10 mg/kg) |
| 58 | "A" | nd | 62% (10 mg/kg) |
| 59 | "A" | nd | 75% (10 mg/kg) |
| 60 | "A" | 5.2 | 50% (10 mg/kg) |
| 61 | "D" | nd | nd |
| 62-trans | "D" | 3.3 | 100% (40 mg/kg) |
| 62-cis | "D" | 6.9 | 63% (40 mg/kg) |
| 63 | "A" | 0.7 | 75% (20 & 40 mg/kg) |
| 64 | "A" | nd | 83% (5 & 20 mg/kg) |
| 65 | "A" | 3.2 | 62% (10 mg/kg) |

[a]$D_2$ Binding
A: $IC_{50}$ = 1,000–10,000 nM
B: $IC_{50}$ = 10,000–50,000 nM
C: $IC_{50}$ = 50,000–100,000 nM
D: $IC_{50}$ = >100,000 nM
[b]nd = not determined The compounds of the present invention are selective agents at the sigma receptor. It has been suggested that specific sigma antagonists are an interesting approach in the development of new anti-ischemic agents [see: D. Lobner and P. Lipton: *Neurosci. Lett.* 117, 169–174 (1990); and T. S. Rao, et. al., *Neuropharmacology* 29, 1199–1204 (1990b)]. Furthermore, there is evidence that sigma agents may be useful in the treatment of psychosis [see: Su, T.-P.: *Neurosci. Lett.* 71: 224–228 (1986)]. Compounds of the present invention are thus envisioned to be useful in the treatment of psychosis, as well as in the treatment of brain ischemia.

In vitro $IC_{50}$ test values for binding to the sigma receptor were determined for representative compounds of Formula I by the method of Tam and Cook [see: Tam, S. W., and Cook, L: *Proc. Natl. Acad. Sci. USA* 81, 5618–5621 (1984)] with only minor modifications. Test $IC_{50}$ values lower than 100 nM are considered to reflect activity at the sigma receptor. Compounds with $IC_{50}$ values lower than 40 nM comprise the preferred compounds.

The anoxic nitrogen test is an in vivo model of brain ischemia in rats [see: Wauquire, A., et al: *Arch. Int. Pharmacodyn.*, 249, 330–334 (1981); Wauquier, A., et al: *Drug Dev. Res.*, 8, 373–380 (1986)]. Compounds of the present invention are active in this in vivo model of brain ischemia when given subcutaneously in the doses indicated in Table 2, thus providing additional evidence that the present compounds will be useful in the treatment of brain ischemia.

It is also known that agents which interact with dopaminergic receptors can produce movement disorders and other extrapyramidal side effects (see: R. J. Baldessarini, Drugs and the Treatment of Psychiatric Disorders, in *Goodman and Gilmans: The Pharmacologic Basis of Therapeutics*, 8th ed., p. 428, A. G. Goodman, T. W. Rall, A. S. Nies, and P. Taylor, Editors, Pergamon Press, Inc., Fairview Park, N.Y., 1990). The compounds claimed herein are inactive at the dopaminergic receptors at the doses used to treat disorders such as anxiety, thus the risk of extrapyramidal side effects is small.

In vitro $IC_{50}$ test values for binding to the $D_2$ receptor were determined for representative compounds of Formula I by the method of Burt, Creese, and Snyder, *Molecular Pharmacology* 12, 800 (1976); Creese, Burt, and Snyder, Science 196, 326 (1977); and Creese, Burt and Snyder, Science 192, 481 (1976). Test IC$_{50}$ values greater than 1,000 nM are considered to reflect inactivity at the D$_2$ receptor, indicating the risk of extrapyramidal side effects is small. Compounds with IC$_{50}$ values greater than 1,000 nM comprise the preferred compounds.

Reasonable variations, such as those which would occur to a skilled artisan, may be made herein without departing from the scope of the invention.

We claim:

1. A non-dopaminergic compound of Formula I or a pharmaceutically acceptable salt or hydrate thereof:

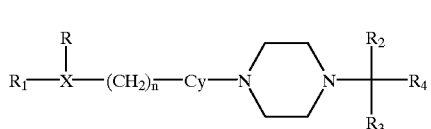

(I)

wherein
R=R$_1$ and is independently H, C$_{1-4}$ alkyl, C$_{1-4}$ alkoxy, C$_{1-4}$ trihaloalkyl or halogen, or R and R$_1$ may be taken together to form an —O(CH$_2$)$_m$O— (m=1 or 2);
X=a 3-indolyl, phenyl, naphthalenyl or 2-benzothiazolyl residue;
n=0, 1, 2 or 3;

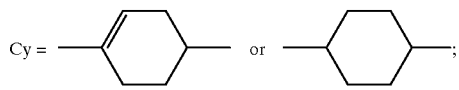

R$_2$=R$_3$ and is independently H or C$_{1-4}$ alkyl; and
R$_4$=phenyl, 2-thienyl, 2-quinolinyl, 4-pyridinyl or substituted phenyl
wherein the phenyl group is mono-, di- or tri-substituted with groups selected from: F, Br, Cl, I and C$_{14}$ alkoxy.

2. The compound of claim 1 wherein R$_2$ and R$_3$ are both H.

3. The compound of claim 2 wherein R$_4$ is phenyl, 2-thienyl, 2-quinolinyl, or 4-pyridinyl.

4. The compound of claim 2 wherein R$_4$ is a mono- or disubstituted phenyl moiety.

5. The compound of claim 2 wherein Cy is the 1-cyclohexenyl residue.

6. The compound of claim 5 selected from the group consisting of:
1-[4-(4-fluorophenyl)-3-cyclohexen-1-yl]-4-(phenylmethyl) piperazine;
1-[4-(4-fluoro-1-naphthalenyl)-3-cyclohexen-1-yl]-4-(phenylmethyl)-piperazine;
1-[4-(1,3-benzodioxol-5-yl)-3-cyclohexen-1-yl]-4-(phenylmethyl)-piperazine;
1-[4-(2-benzothiazolyl)-3-cyclohexen-1-yl]-4-(phenylmethyl)piperazine;
1-[4-(4-methoxyphenyl)-3-cyclohexen-1-yl]-4-(phenylmethyl)piperazine;
1-(phenylmethyl)-4-[4-[4-(trifluoromethyl)phenyl]-3-cyclohexen-1-yl]-piperazine;
1-[4-(4-(fluorophenyl)-3-cyclohexen-1-yl]-4-[(4-fluorophenyl)methyl]-piperazine;
1-[(4-fluorophenyl)methyl]-4-{4-[(4-trifluoromethyl)phenyl]-3-cyclohexen-1-yl}piperazine;
1-(phenylmethyl)-4-[4-(phenylmethyl)-3-cyclohexen-1-yl] piperazine;
1-[4-(4-fluorophenyl)-3-cyclohexen-1-yl]-4-(2-thienylmethyl)piperazine;
2[[4-[4-(4-fluorophenyl)-3-cyclohexen-1-yl]-1-piperazinyl] methyl]quinoline;
1-[4-(4-fluorophenyl)-3-cyclohexen-1-yl]-4-(4-pyridinylmethyl)piperazine;
5-methoxy-3-(4-[4-(phenylmethyl)-1-piperazinyl]-1-cyclohexen-1-yl]-1H-indole;
5-fluoro-3-{4-[4-(phenylmethyl)-1-piperazinyl]-1-cyclohexen-1-yl}-1H-indole;
5-chloro-3-[4-[4-(phenylmethyl)-1-piperazinyl]-1-cyclohexen-1-yl]-1H-indole;
1-[4-(1,4-benzodioxan-6-yl)-3-cyclohexen-1-yl]-4-(phenylmethyl)piperazine;
1-[4-(1,3-benzodioxol-5-yl)-3-cyclohexen-1-yl]-4-[(2-chlorophenyl)methyl]-piperazine;
1-[4-(1,3-benzodioxol-5-yl)-3-cyclohexen-1-yl]-4-[(2,5-difluorophenyl)methyl]-piperazine;
1-[4-(1,3-benzodioxol-5-yl)-3-cyclohexen-1-yl]-4-[(3-methoxyphenyl)methyl]-piperazine;
1-[(4-fluorophenyl)-3-cyclohexen-1-yl]-4-[(3-methoxyphenyl)methyl]-piperazine; and
1-[4-(1,3-benzodioxol-5-yl)-3-cyclohexen-1-yl]-4-[(2,5-diiodophenyl)methyl]-piperazine.

7. The compound of claim 2 wherein Cy is the cyclohexyl residue.

8. The compound of claim 7 selected from the group consisting of:
cis 1-[4-(4-fluoro-1-naphthalenyl)-1-cyclohexyl]-4-(phenylmethyl)piperazine;
trans 1-[4-(4-fluoro-1-naphthalenyl)-1-cyclohexyl]-4-(phenylmethyl)piperazine;
trans 1-[4-(4-fluorophenyl)-1-cyclohexyl]-4-(phenylmethyl)piperazine;
trans 2-[[4-[4-(4-fluorophenyl)-1-cyclohexyl]-1-piperazinyl]methyl]quinoline; and
trans 1-[4-(4-fluorophenyl)-1-cyclohexyl]-4-[(3-methoxyphenyl)methyl]piperazine.

9. A pharmaceutical composition comprising an effective anti-ischemia amount of a non-dopominergic compound of claim 1 and a pharmaceutically acceptable carrier.

10. The composition of claim 9 wherein the compound is one in which R$_2$ and R$_3$ are both H.

11. The composition of claim 10 wherein R$_4$ is phenyl, 2-thienyl, 2-quinolinyl, or 4-pyridinyl.

12. The composition of claim 10 wherein R$_4$ is a mono- or di-substituted phenyl moiety.

13. The composition of claim 10 wherein the compound is selected from the group consisting of:
1-[4-(4-fluorophenyl)-3-cyclohexen-1-yl]-4-(phenylmethyl) piperazine;
1-[4-(4-fluoro-1-naphthalenyl)-3-cyclohexen-1-yl]-4-(phenylmethyl)-piperazine;
1-[4-(1,3-benzodioxol-5-yl)-3-cyclohexen-1-yl]-4-(phenylmethyl)-piperazine;
1-[4-(2-benzothiazolyl)-3-cyclohexen-1-yl]-4-(phenylmethyl)piperazine;
1-[4-(4-methoxyphenyl)-3-cyclohexen-1-yl]-4-(phenylmethyl)piperazine;
1-(phenylmethyl)-4-[4-[4-(trifluoromethyl)phenyl]-3-cyclohexen-1-yl]-piperazine;
1-[4-(4-(fluorophenyl)-3-cyclohexen-1-yl]-4-[(4-fluorophenyl)methyl]-piperazine;
1-[(4-fluorophenyl)methyl]-4-[4[(4-trifluoromethyl) phenyl]-3-cyclohexen-1-yl]piperazine;
1-(phenylmethyl)-4-[4-(phenylmethyl)-3-cyclohexen-1-yl] piperazine;

1-[4-(4-fluorophenyl)-3-cyclohexen-1-yl]-4-(2-thienylmethyl)piperazine;
2[[4-[4-(4-fluorophenyl)-3-cyclohexen-1-yl]-1-piperazinyl]methyl]-quinoline;
1-[4-(4-fluorophenyl)-3-cyclohexen-1-yl]-4-(4-pyridinylmethyl)-piperazine;
5-methoxy-3-[4-[4-(phenylmethyl)-1-piperazinyl]-1-cyclohexen-1-yl]-1H-indole;
5-fluoro-3-[4-[4-(phenylmethyl)-1-piperazinyl]-1-cyclohexen-1-yl]-1H-indole;
5-chloro-3-[4-[4-(phenylmethyl)-1-piperazinyl]-1-cyclohexen-1-yl]-1H-indole;
5-fluoro-3-[4-[4-(phenylmethyl)-1-piperazinyl]-1-cyclohexen-1-yl]-1H-indole;
1-[4-(1,4-benzodioxan-6-yl)-3-cyclohexen-1-yl]-4-(phenylmethyl)-piperazine;
1-[4-(1,3-benzodioxol-5-yl)-3-cyclohexen-1-yl]-4-[(2-chlorophenyl)-methyl]piperazine;
1-[4-(1,3-benzodioxol-5-yl)-3-cyclohexen-1-yl]-4-[(2,5-difluorophenyl)-methyl]-piperazine;
1-[4-(1,3-benzodioxol-5-yl)-3-cyclohexen-1-yl]-4-[(3-methoxyphenyl)-methyl]-piperazine;
1-[(4-fluorophenyl)-3-cyclohexen-1-yl]-4-[(3-methoxyphenyl)methyl]-piperazine; and
1-[4-(1,3-benzodioxol-5-yl)-3-cyclohexen-1-yl]-4-[(2,5-diiodophenyl)-methyl]-piperazine.

14. The composition of claim 9 wherein the compound is selected from the group consisting of:
cis 1-[4-(4-fluoro-1-naphthalenyl)-1-cyclohexyl]-4-(phenylmethyl)piperazine;
trans 1-[4-(4-fluoro-1-naphthalenyl)-1-cyclohexyl]-4-(phenylmethyl)piperazine;
trans 1-[4-(4-fluorophenyl)-1-cyclohexyl]-4-(phenylmethyl)piperazine;
trans 2-[[4-[4-(4-fluorophenyl)-1-cyclohexyl]-1-piperazinyl]methyl]quinoline; and
trans 1-[4-(4-fluorophenyl)-1-cyclohexyl]-4-[(3-methoxyphenyl) methyl]piperazine.

15. A process for treating ischemia-induced brain disorders in a mammal in need of such treatment, the treatment comprising of administering to the mammal an effective non-dopaminergic amount of a compound of claim 1.

16. The process of claim 15 wherein the compound is one in which $R_2$ and $R_3$ are both H.

17. The process of claim 16 wherein R, is phenyl, 2-thienyl, 2-quinolinyl, or 4-pyridinyl.

18. The process of claim 16 wherein $R_4$ is a mono- or di-substituted phenyl moiety.

19. The process of claim 16 wherein the compound is selected from the group consisting of:
cis 1-[4-(4-fluoro-1-naphthalenyl)-1-cyclohexyl]-4-(phenylmethyl)piperazine;
trans 1-[4-(4-fluoro-1-naphthalenyl)-1-cyclohexyl]-4-(phenylmethyl)piperazine;
trans 1-[4-(4-fluorophenyl)-1-cyclohexyl]-4-(phenylmethyl)piperazine;
trans 2-[[4-[4-(4-fluorophenyl)-1-cyclohexyl]-1-piperazinyl}-methyl}quinoline; and
trans 1-[4-(4-fluorophenyl)-1-cyclohexyl]-4-[(3-methoxyphenyl)methyl]piperazine.

20. The process of claim 16 wherein the compound is selected from the group consisting of:
1-[4-(4-fluorophenyl)-3-cyclohexen-1-yl]-4-(phenylmethyl)piperazine;
1-[4-(4-fluoro-1-naphthalenyl)-3-cyclohexen-1-yl]-4-(phenylmethyl)-piperazine;
1-[4-(1,3-benzodioxol-5-yl)-3-cyclohexen-1-yl]-4-(phenylmethyl)-piperazine;
1-[4-(2-benzothiazolyl)-3-cyclohexen-1-yl]-4-(phenylmethyl)piperazine;
1-[4-(4-methoxyphenyl)-3-cyclohexen-1-yl]-4-(phenylmethyl)piperazine;
1-(phenylmethyl)-4-[4-[4(trifluoromethyl)phenyl]-3-cyclohexen-1-yl]-piperazine;
1-[4-(4-(fluorophenyl)-3-cyclohexen-1-yl]-4-[(4-fluorophenyl)methyl]-piperazine;
1-[(4-fluorophenyl)methyl]-4-{4-[(4-trifluoromethyl)phenyl]-3-cyclohexen-1-yl]piperazine;
1-(phenylmethyl)-4-[4-(phenylmethyl)-3-cyclohexen-1-yl]piperazine;
1-[4-(4-fluorophenyl)-3-cyclohexen-1-yl]-4-(2-thienylmethyl)piperazine;
2[[4-[4-(4-fluorophenyl)-3-cyclohexen-1-yl]-1-piperazinyl]methyl]-quinoline;
1-[4-(4-fluorophenyl)-3-cyclohexen-1-yl]-4-(4-pyridinylmethyl)-piperazine;
5-methoxy-3-[4-[4-(phenylmethyl)-1-piperazinyl]-1-cyclohexen-1-yl]-1H-indole;
5-fluoro-3-[4-[4-(phenylmethyl)-1-piperazinyl]-1-cyclohexen-1-yl]-1H-indole;
5-chloro-3-[4-[4-(phenylmethyl)-1-piperazinyl]-1-cyclohexen-1-yl]-1H-indole;
1-[4-(1,4-benzodiox-6-yl)-3-cyclohexen-1-yl]-4-(phenylmethyl)piperazine;
1-[4-(1,3-benzodioxol-5-yl)-3-cyclohexen-1-yl]-4-[(2-chlorophenyl)-methyl]-piperazine;
1-[4-(1,3-benzodioxol-5-yl)-3-cyclohexen-1-yl]-4-[(2,5-difluorophenyl)-methyl]-piperazine;
1-[4-(1,3-benzodioxol-5-yl)-3-cyclohexen-1-yl]-4-[(3-methoxyphenyl)-methyl]-piperazine;
1-[(4-fluorophenyl)-3-cyclohexen-1-yl]-4-[(3-methoxyphenyl)methyl]-piperazine; and
1-[4-(1,3-benzodioxol-5-yl)-3-cyclohexen-1-yl]-4-[(2,5-diiodophenyl)-methyl]-piperazine.

* * * * *